US012623304B2

(12) United States Patent
Gebert et al.

(10) Patent No.: US 12,623,304 B2
(45) Date of Patent: May 12, 2026

(54) METHOD FOR PREPARING A PROCESSED FILAMENT BY INTERACTION OF A FILAMENT WITH AT LEAST ONE PROCESSING BEAM IN N PROCESSING STEPS

(71) Applicants: Heraeus Deutschland Gmbh & Co. KG, Hanau (DE); Heraeus Medical Components LLC, St. Paul, MN (US)

(72) Inventors: Joerg-Martin Gebert, Hanau (DE); Paul Schuster, St. Paul, MN (US); Yang Yu, Singapore (SG)

(73) Assignees: Heraeus Medical Components LLC, St. Paul, MN (US); Heraeus Medevio GmbH & Co. KG, Hanau (DE)

( * ) Notice: Subject to any disclaimer, the term of this patent is extended or adjusted under 35 U.S.C. 154(b) by 561 days.

(21) Appl. No.: 16/939,774

(22) Filed: Jul. 27, 2020

(65) Prior Publication Data

US 2021/0023657 A1      Jan. 28, 2021

Related U.S. Application Data

(60) Provisional application No. 62/879,189, filed on Jul. 26, 2019.

(51) Int. Cl.
*B23K 26/36* (2014.01)
*B23K 26/352* (2014.01)
(Continued)

(52) U.S. Cl.
CPC ............ *B23K 26/36* (2013.01); *B23K 26/355* (2018.08); *B23K 26/362* (2013.01);
(Continued)

(58) Field of Classification Search
CPC ................ B23K 26/36; B23K 2101/32; B23K 2101/34; B23K 26/355; B23K 26/362
See application file for complete search history.

(56) References Cited

U.S. PATENT DOCUMENTS

| | | | |
|---|---|---|---|
| 5,515,848 A | 5/1996 | Corbett, III et al. | |
| 7,903,336 B2 * | 3/2011 | Pelsue .................. | B23K 26/364 |
| | | | 250/237 G |

(Continued)

FOREIGN PATENT DOCUMENTS

| | | |
|---|---|---|
| WO | 01/13102 | 2/2001 |
| WO | 2015/156966 | 10/2015 |

*Primary Examiner* — Steven W Crabb
*Assistant Examiner* — Fahmida Ferdousi
(74) *Attorney, Agent, or Firm* — Dicke, Billig & Czaja, PLLC

(57) ABSTRACT

One aspect refers to a method for preparing a processed filament, including providing a filament, which comprises a multitude of segments, which follow one another in a longitudinal direction of the filament, wherein each of the segments of the multitude of segments comprises a multitude of sections, which are disposed circumferentially around the filament; and processing the filament in n processing steps, thereby obtaining the processed filament. For each integer i in the range from 1 to n, the $i^{th}$ processing step comprises, for each integer j in the range from 1 to m, processing the $j^{th}$ section of the $(i+j-1)^{th}$ segment. N and m are integers which are, independent from one another, at least 2. Sections of different number are at different circumferential locations of the filament. The processing of each section of each segment of the filament comprises an interaction of the section of the segment of the filament with at least one processing beam.

9 Claims, 21 Drawing Sheets

(51) Int. Cl.

| | |
|---|---|
| B23K 26/362 | (2014.01) |
| B23K 101/32 | (2006.01) |
| B23K 101/34 | (2006.01) |
| *A61B 5/1486* | (2006.01) |

(52) U.S. Cl.

CPC ....... *A61B 5/14865* (2013.01); *B23K 2101/32* (2018.08); *B23K 2101/34* (2018.08)

(56) References Cited

U.S. PATENT DOCUMENTS

| | | | |
|---|---|---|---|
| 8,755,654 B1* | 6/2014 | Danley ................. | G02B 6/245 |
| | | | 385/43 |
| 9,132,585 B2 | 9/2015 | Miller et al. | |
| 9,401,266 B2* | 7/2016 | Splendore ............ | H01J 49/147 |
| 10,399,184 B2* | 9/2019 | Hosseini ........... | B23K 26/0624 |
| 2011/0230735 A1 | 9/2011 | Wolfe et al. | |
| 2013/0245412 A1* | 9/2013 | Rong ................ | A61B 5/14532 |
| | | | 600/347 |
| 2018/0186678 A1* | 7/2018 | Boeker ................ | C03B 33/093 |

* cited by examiner

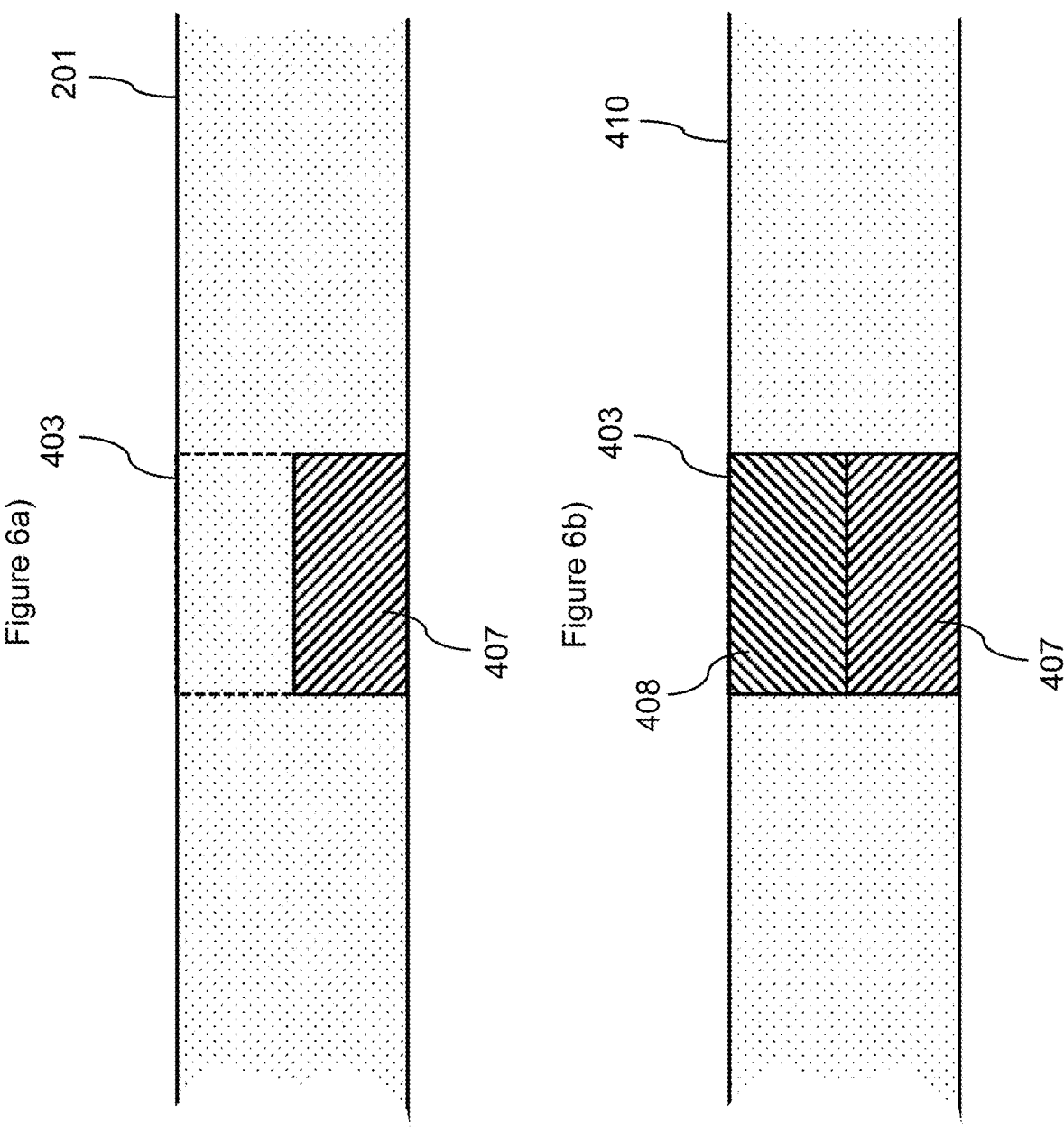

100

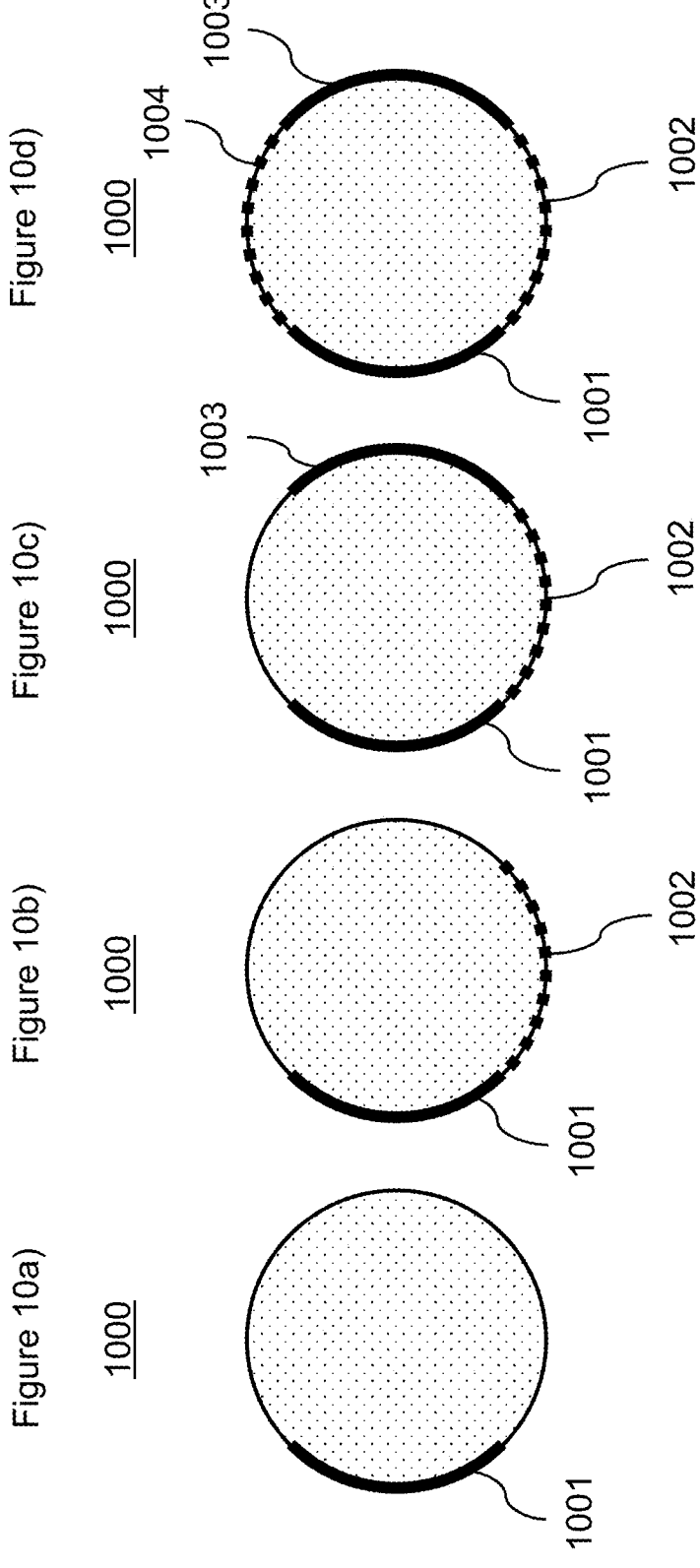

METHOD FOR PREPARING A PROCESSED FILAMENT BY INTERACTION OF A FILAMENT WITH AT LEAST ONE PROCESSING BEAM IN N PROCESSING STEPS

CROSS-REFERENCED TO RELATED APPLICATION

This Non-Provisional Patent Application claims the benefit of the filing date of U.S. Provisional Patent Application Ser. No. 62/879,189, filed Jul. 26, 2019, which is incorporated herein by reference.

TECHNICAL FIELD

One aspect relates to a process for preparing a processed filament,

SUMMARY

One aspect is a including providing a filament, which comprises a multitude of segments, which follow one another in a longitudinal direction of the filament, wherein each of the segments of the multitude of segments comprises a multitude of sections, which are disposed circumferentially around the filament, and processing the filament in n processing steps, thereby obtaining the processed filament. For each integer i in the range from 1 to n, the $i^{th}$ processing step comprises, for each integer j in the range from 1 to m, processing the $i^{th}$ section of the $(i+j-1)^{th}$ segment, wherein n and m are integers which are, independent from one another, at least 2. Sections of different number are at different circumferential locations of the filament. The processing of each section of each segment of the filament comprises an interaction of the section of the segment of the filament with at least one processing beam. One aspect related to a processed filament, obtainable by the process; to an electrical device, including at least a part of the processed filament; to devices for preparing a processed filament; to a use of at least one laser; and to a use of a filament for being processed.

BACKGROUND

Thin multilayer wires are used in applications such as electrochemical sensors. Such wires often include a metal core, a polymer coating and an outer metal coating. Preparing the wire for manufacture of an electrochemical sensor includes removal of the outer metal layer across defined segments of the wire which are then coated with enzymes. In the prior art, removal of the outer metal layer by high-precision laser ablation is known. Therein, the longitudinal positions of the wire (segments) are ablated one after the other (sequentially). This is done because the laser introduces a considerable amount of heat to the wire. Overheating of the wire may, however, damage parts of the wire which are not meant to be altered by the ablation process. Such damages may affect the quality of the electrochemical sensor which includes such a wire. Accordingly, such damages have to be avoided. Nevertheless, there is a strong need for higher production rates. In result, there is room for improvement of laser ablation processes of the prior art.

From the results of the comparative examples 1 to 3, it can be seen that there is a trade-off between high process speed, i.e. high production rate, and the goal to avoid damages to the PU-layer, i.e. a high quality of processed wires. Here, it should be considered that damaging the PU-layer means to partially structure the outer surface of the PU-layer. In result, a surface tension of the outer surface of the PU-layer is not uniform across the exposed region of the PU-layer. In preparing an electrochemical sensor, this may lead to non-uniform coating thicknesses of enzyme layers on the wire. The signal-to-noise ratio of the sensor as well as the linearity of the sensor response may suffer in result. Hence, in the technical field of the invention, the above trade-off is between high production rates and high accuracies of electrochemical sensors. This trade-off is resolved in the examples 1 and 2. Hence, the process according to one embodiment allows to produce wires for high accuracy electrochemical sensors at a high production rate.

Generally, it is an object of the present embodiments to at least partly overcome a disadvantage arising from the prior art.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

The figures show, in schematic form and not to scale, unless stated otherwise in the description or the respective figure:

FIG. 3 a scheme for illustration of a general processing step of the process of FIG. 1;

FIG. 6a) a side view of the second segment of the filament after the first processing step of the process of FIG. 1;

FIG. 6b) a side view of the second segment of the processed filament after the second processing step of the process of FIG. 1;

FIG. 10*a*) a cross-section through the fourth segment of the filament after the first processing step of the process of FIG. 7;

FIG. 10*b*) a cross-section through the fourth segment of the filament after the second processing step of the process of FIG. 7;

FIG. 10*c*) a cross-section through the fourth segment of the filament after the third processing step of the process of FIG. 7;

FIG. 10*d*) a cross-section through the fourth segment of the filament after the fourth processing step of the process of FIG. 7;

FIG. 16 an electrical device according to one embodiment;

DETAILED DESCRIPTION

Figure 1:
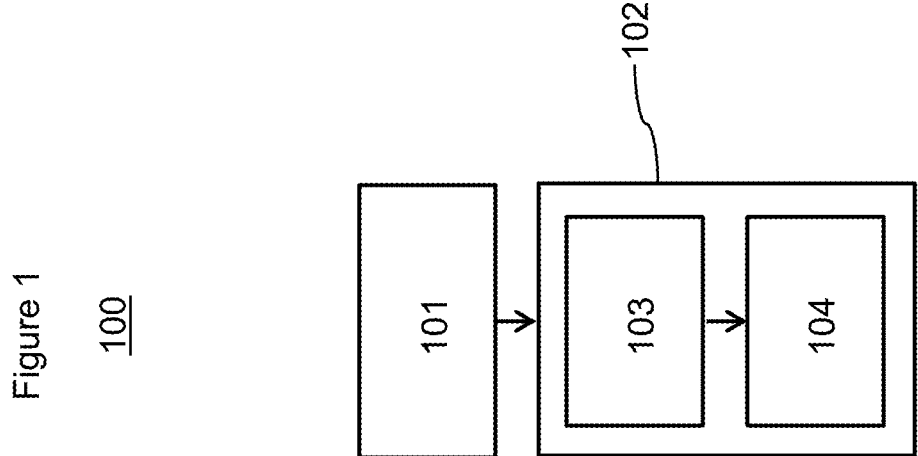
FIG. 1 a flow-chart of a process according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

It is a further object of one embodiment to provide a process and/or device for preparing a multilayer wire for manufacturing an electrochemical sensor of as high as possible accuracy at an as high as possible production rate.

Therein, the sensor accuracy, in one embodiment, refers to a signal-to-noise-ratio of the sensor or a linearity of a sensor response or both. Further, it is an object of one embodiment to provide a process and/or device for preparing a multilayer wire for manufacturing an electrochemical sensor, wherein a polymer layer of the wire or a metal core of the wire or both is as far as possible not damaged in the course of preparing the wire. According to a further object of one embodiment, one of the above processes and/or devices is provided, wherein the process/device is as simple as possible. It is a further object of one embodiment to provide a thin multilayer wire which is particularly suitable for manufacturing an electrochemical sensor of as high as possible accuracy, wherein the wire is obtainable at an as high as possible production rate.

A contribution to at least one of the above objects is given by the independent claims. The dependent claims provide embodiments of the present embodiments which also serve solving at least one of the above mentioned objects.

A contribution to the solution of at least one of the above objects is provided by an embodiment 1 of a process, according to one embodiment, for preparing a processed filament, the process including as process steps a) providing a filament, which comprises a multitude of segments, which follow one another in a longitudinal direction of the filament, wherein each of the segments of the multitude of segments comprises a multitude of sections, which are disposed circumferentially around the filament; and b) processing the filament in n processing steps, thereby obtaining the processed filament;

wherein for each integer i in the range from 1 to n, the $i^{th}$ processing step comprises, for each integer j in the range from 1 to m, processing the $j^{th}$ section of the $(i+j-1)^{th}$ segment; wherein n and m are integers which are, independent from one another, at least 2; wherein sections of different number are at different circumferential locations of the filament; wherein the processing of each section of each segment of the filament comprises an interaction of the section of the segment of the filament with at least one processing beam. In one embodiment, each of the segments of the multitude of segments consists of m sections. In one embodiment, the segments of the multitude of segments are spaced apart from one another in the longitudinal direction of the filament, i.e. between consecutive segments there is some length of the filament which is not a segment of the multitude of segments. This means that the segments of the multitude of segments, in one embodiment, do not sum up to the whole length of the filament. Herein, the term "processed filament" does not necessarily imply that an end product has been obtained. Hence, the processed filament may or may not be further processed, i.e. the processed filament may or may not be an intermediate product. This intermediate product may be processed further in the process or in a subsequent process. In one embodiment, in each of the n processing steps, each of the m sections is processed by another processing beam. Therein, the processing beams, in one embodiment, have one selected from the group consisting of the same spectrum, the same fluence, the same energy per pulse, the same pulse frequency, and the same focal spot size, or a combination of at least two thereof. In one embodiment, the processing beams are identical. In one embodiment, the processing beams are provided by the same processing beam source. In another preferred embodiment, at least two of the processing beams are provided by different processing beam sources. Therein, the different processing beam sources are, in one embodiment, identical.

In one embodiment, the process is conducted with the device 1 according one embodiment or with the device 2 according to one embodiment.

Herein, n and m are indices which are independent from one another. n defines the number of processing which are described by the above. The process may, however, comprise further processing steps, i.e. more than n processing steps. m defines the number sections per segment which is processed in the n processing steps as described above. i is a running variable which runs from 1 to n. Accordingly, i is used to denote single processing steps of the n processing steps. j is a running variable which, for each of the n processing steps, runs from 1 to m. j is used to denote single sections of a segment and also to denote the respective segment. Accordingly, the characters "n", "m", "i" and "j" are not abbreviations and do not have any meaning other than being characters to identify the respective index or running variable. The sections of a segment may or may not follow one another around the circumference of the segment in the order of their numbers. The segments of the filament may or may not follow one another in the longitudinal direction of the filament in the order of their numbers. In one embodiment, the segments of the filament do follow one another in the longitudinal direction of the filament in the order of their numbers.

Herein, process steps which follow one another in the order of the characters denoting the steps may follow one another directly or indirectly in time, i.e. there may be a further process step in-between or not. Further, the process steps, which follow one another in the order of the characters denoting the steps, may be conducted one after the other, in partial temporal overlap or simultaneously. In one embodiment, the processing steps are conducted one after the other in the order of their numbers. Herein, the term multitude means that there are at least two items which form the multitude of items. Further, herein subsequent items may follow one another directly or indirectly. Consecutive items, on the other hand, mandatorily follow one another directly. In case of items following one another directly, there is no such item in-between. There may, however, be items of another kind in-between. For example, 2 segments may follow one another directly. This means that there is no segment of the multitude of segments in-between. This does, however, not imply that the 2 segments adjoin one another.

The process, in one embodiment, further comprises creating an image, in one embodiment a sequence of images, of a segment that has been processed, in one embodiment at m sections, in the process step b). This may be conducted in the process step b) or after the process step b). In one embodiment, the image, in one embodiment the sequence of images, of the segment is captured.

In its embodiment 2, the process is configured according to its embodiment 1, wherein, in each $i^{th}$ processing step, the processing of the $1^{st}$ to $m^{th}$ sections is conducted at least in temporal overlap, in one embodiment simultaneously, with one another. Here, the m sections, which are processed in each of the n processing steps, are processed in temporal overlap or, in one embodiment, simultaneously. Accordingly, there is more than 1 processing beam, in one embodiment m processing beams. In one embodiment, there are m processing beams. In one embodiment, there is at least one processing beam per each segment which is processed in a single processing step.

In its embodiment 3, the process is configured according to its embodiment 1 or 2, wherein n equals m.

In its embodiment 4, the process is configured according to any of its preceding embodiments, wherein the sum of the surface areas of the sections of a segment, which are processed in the process step b), equals the surface area of an outer surface of this segment. In one embodiment, for each segment of the multitude of segments, all the sections of the segment are equidistantly disposed around the circumference of the respective segment in terms of an angular distance between neighbouring sections along the circumference. In one embodiment, the surface areas of m sections of each of the segments of the multitude of segments, for each of these segments, sum up the surface area of an outer surface of the respective segment. Additionally or alternatively preferred, for each of the segments of the multitude of segments, m sections cover the whole circumference of the respective segment. Additionally or alternatively preferred, for each of the segments of the multitude of segments, the m sections are of equal circumferential span. In other words, it is preferred that each of the segments of the multitude of segments consists of m sections, wherein each of these sections covers 360°/m of a circumference of the respective segment. Additionally or alternatively preferred, for each segment of the multitude of segments, all the sections of the segment are adjacent to one another. In one embodiment, for each segment of the multitude of segments, all the sections of the segment are equidistantly disposed around the circumference of the respective segment in terms of an angular distance between neighbouring sections along the circumference.

In its embodiment 5, the process is configured according to any of its preceding embodiments, wherein n or m or each of both is at least 3, in one embodiment at least 4, in one embodiment exactly 4. In some cases, n or m or each of both may even be more than 4. In a particularly preferred embodiment m and n are each exactly 4.

In its embodiment 6, the process is configured according to any of its preceding embodiments, wherein the segments of the multitude of segments are disposed equidistantly to one another along a length of the filament.

In its embodiment 7, the process is configured according to any of its preceding embodiments, wherein between each of two consecutive processing steps the filament is moved in a direction of its length. In one embodiment, the filament is moved by a distance which is a distance between neighbouring segments of the multitude of segments. Therein, the distance is, in one embodiment, measure in a centre-to-centre manner. A preferred kind of moving is a shifting.

In its embodiment 8, the process is configured according to any of its preceding embodiments, wherein the at least one processing beam is at least one beam of particles or at least one beam of electromagnetic radiation or at least one beam of both. In the latter case, there may be at least one beam of particles and at least one beam of electromagnetic radiation, or at least one beam which is a combination of a beam of particles and a beam of electromagnetic radiation. A beam of particles may, for example, be a beam of electrons or a beam of ions or both, for example a plasma beam. Preferred electromagnetic radiation of a beam of electromagnetic radiation has a spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm.

In its embodiment 9, the process is configured according to any of its preceding embodiments, wherein the filament comprises a. a core, including a first metal, b. a first layer which i. is superimposed on the core, and ii. comprises a polymer, and c. a second layer which i. is superimposed on the first layer, and ii. comprises a second metal.

In its embodiment 10, the process is configured according to its embodiment 9, wherein the second metal is different from the first metal.

In its embodiment 11, the process is configured according to its embodiment 9 or 10, wherein the first metal is one selected from the group consisting of platinum, tantalum, and palladium, or an alloy including one of the preceding metals. A preferred alloy including platinum is platinum iridium or platinum tungsten. A preferred alloy including tantalum is tantalum niobium or tantalum tungsten.

In its embodiment 12, the process is configured according to any of its embodiments 9 to 11, wherein the second metal is silver. In one embodiment, the second layer further comprises a salt of the second metal. A preferred salt of silver is AgCl.

In its embodiment 13, the process is configured according to any of its embodiments 9 to 12, wherein the polymer is one selected from the group consisting of a poly-addition product, a poly-condensation product, and one or more polysiloxanes, or a combination of at least two thereof. A preferred poly-addition product is polyurethane or a poly-olefin. A preferred poly-condensation product is one selected from the group consisting of polyimide, polyamide, and polyethylene terephthalate, or a combination of at least two thereof. A preferred polyolefin is polyethylene or polypropylene. A further preferred polymer is a thermoplastic polymer. A particularly preferred polymer is polyurethane.

In its embodiment 14, the process is configured according to any of its preceding embodiments, wherein the processing in the processing steps is a, in one embodiment exclusively, subtractive process, as opposed to an additive process, such as welding.

In its embodiment 15, the process is configured according to any of its embodiments 9 to 14, wherein the processing in the processing steps comprises at least partially, in one embodiment completely, removing the second layer from the sections of the segments of the multitude of segments.

In its embodiment 16, the process is configured according to its embodiment 15, wherein, in the processing steps, at least partially, in one embodiment completely, removing the second layer comprises ablation. Ablation is removal of material from the surface of an object by vaporisation, chipping, or other erosive processes. A preferred ablation is laser-ablation.

In its embodiment 17, the process is configured according to any of its preceding embodiments, wherein the filament has a length in range from 10 m to 10 km, in one embodiment from 100 to 8 km, and in one embodiment from 500 m to 5 km.

In its embodiment 18, the process is configured according to any of its preceding embodiments, wherein the filament has a diameter in the range from 0.1 to 1.0 mm, in one embodiment from 0.1 to 0.8 mm, in one embodiment from 0.1 to 0.6 mm, and in one embodiment from 0.12 to 0.4 mm.

In its embodiment 19, the process is configured according to any of its preceding embodiments, wherein the filament is one selected from the group consisting of a wire, a cable, and a fibre, or a combination of at least two thereof. A preferred fibre is an optical fibre. A particularly preferred filament is a wire.

In its embodiment 20, the process is configured according to any of its embodiments 9 to 19, wherein a thickness of the second layer is in the range from 1 to 25 μm, in one embodiment from 2 to 20 μm, in one embodiment from 3 to 17 μm, and in one embodiment from 5 to 15 μm.

In its embodiment 21, the process is configured according to any of its preceding embodiments, wherein the at least one processing beam is at least one laser beam. The at least one laser beam, in one embodiment, has a spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm.

In its embodiment 22, the process is configured according to its embodiment 21, wherein the at least one laser beam is at least one pulsed laser beam, as opposed to at least one continuous layer beam.

In its embodiment 23, the process is configured according to its embodiment 22, wherein the at least one pulsed laser beam is characterised by a pulse duration in a range from 10 fs to 500 ns, in one embodiment from 50 fs to 400 ns, in one embodiment from 100 fs to 300 ns, in one embodiment from 500 fs to 200 ns, in one embodiment from 1 to 100 ns, in one embodiment from 10 to 100 ns, and in one embodiment from 15 to 80 ns.

In its embodiment 24, the process is configured according to its embodiment 22 or 23, wherein a fluence of the at least one pulsed laser beam is in the range from 1.0 to 5.0 J/cm$^2$ per pulse, in one embodiment from 1.5 to 4.5 J/cm$^2$ per pulse, in one embodiment from 2.0 to 4.0 J/cm$^2$ per pulse, and in one embodiment from 2.5 to 3.8 J/cm$^2$ per pulse.

In its embodiment 25, the process is configured according to any of its preceding embodiments, wherein the processing in the processing steps comprises moving at least one spot of the at least one processing beam across the section of the segment.

In its embodiment 26, the process is configured according to its embodiment 25, wherein the at least one spot is of a size in the range from 5 to 50 μm, in one embodiment 5 to 40 μm, in one embodiment 5 to 30 μm, and in one embodiment 10 to 20 μm. A preferred spot is a focal spot. Further in one embodiment, the sport is about circular.

In its embodiment 27, the process is configured according to any of its embodiments 22 to 26, wherein the at least one pulsed laser beam is characterised by an energy per pulse in the range from 2 to 15 μJ, in one embodiment from 2 to 13 μJ, in one embodiment from 3 to 10 μJ, and in one embodiment from 4 to 8 μJ.

In its embodiment 28, the process is configured according to any of its embodiments 22 to 27, wherein the at least one pulsed laser beam is pulsed at a frequency in the range from 5 to 600 kHz, in one embodiment from 10 to 500 kHz, in one embodiment from 20 to 500 kHz, in one embodiment from 30 to 450 kHz, in one embodiment from 40 to 400 kHz, in one embodiment from 50 to 350 kHz, in one embodiment from 80 to 300 kHz, in one embodiment from 90 to 250 kHz, in one embodiment from 100 to 200 kHz, and in one embodiment from 110 to 190 kHz.

In its embodiment 29, the process is configured according to any of its embodiments 21 to 28, wherein the at least one laser beam is obtainable from, in one embodiment emitted by, at least one solid-state laser. A gain medium of the at least one solid-state laser is, in one embodiment, a crystal. A preferred crystal is doped with neodym. A preferred neo-dym-doped crystal comprises yttrium. A preferred crystal which comprises yttrium is selected from the group consisting of Nd:YAG, Nd:Y$_3$Al$_5$, O$_{12}$, and Nd:YVO$_4$. Therein, Nd:YVO$_4$ is preferred in one embodiment.

In its embodiment 30, the process is configured according to any of its preceding embodiments, wherein, in each i$^{th}$ processing step, the processing of the 1$^{st}$ to m$^{th}$ sections comprises sweeping a spot of the at least one processing beam across a surface of each of the 1$^{st}$ to m$^{th}$ sections, in each case in a multitude of linear sweeps. The spot of the at least one processing beam is, in one embodiment, a focal spot of this at least one processing beam. In case of more than one processing beam, there may be more than one spot. In this embodiment, the spot is moved across the surface of the section in a sequence of straight lines (multitude of linear sweeps), thereby scanning the surface with the at least one processing beam. Hence, each linear sweep represents a straight line. Here, the surface of the section is, in one embodiment, an outer surface of the second layer. The surface is, in one embodiment, an entire outer surface of the section.

In its embodiment 31, the process is configured according to its embodiment 30, wherein for each multitude of linear sweeps, the linear sweeps of this multitude of linear sweeps are conducted in the same direction. This case is also referred to as uni-directional processing.

In its embodiment 32, the process is configured according to its embodiment 30, wherein a first fraction of the linear sweeps of at least one of the multitudes of linear sweeps is conducted in a first direction, wherein a further fraction of the linear sweeps of this multitude of linear sweeps is conducted in a further direction, wherein the further direction is opposite to the first direction. This case is also referred to as bi-directional processing.

In its embodiment 33, the process is configured according to any its embodiments 30 to 32, wherein the linear sweeps of at least one of the multitudes of linear sweeps incline angles with a length of the filament in the range from 0 to 30°, in one embodiment from 0 to 20°, in one embodiment from 0 to 10°, and in one embodiment from 0 to 5°. In one embodiment the linear sweeps of the multitude of linear sweeps are parallel to the length of the filament, as oriented in the segment to be processed.

In its embodiment 34, the process is configured according to any its embodiments 30 to 33, wherein the linear sweeps of at least one of the multitudes of linear sweeps incline angles with a length of the filament in the range from 60 to 90°, in one embodiment from 70 to 90°, in one embodiment from 80 to 90°, and in one embodiment from 85 to 90°. In one embodiment the linear sweeps of the multitude of linear sweeps are perpendicular to the length of the filament, as oriented in the segment to be processed.

In its embodiment 35, the process is configured according to any its embodiments 30 to 34, wherein a distance between the linear sweeps of at least one of the multitudes of linear sweeps is in the range from 5 to 50 μm, in one embodiment from 5 to 40 μm, in one embodiment from 5 to 30 μm, in one embodiment from 8 to 20 μm, and in one embodiment from 10 to 20 μm. This distance is determined in a centre-to-centre manner. In the technical field, this distance is often also referred to as pitch.

In its embodiment 36, the process is configured according to any its embodiments 30 to 35, wherein, in the sweeping of the processing steps, the spot moves relative to the surface of the section at a velocity in the range from 100 to 3000 mm/s, in one embodiment from 200 to 2500 mm/s, in one embodiment from 400 to 2000 mm/s, in one embodiment from 600 to 1800 mm/s, and in one embodiment from 800 to 1600 mm/s.

In its embodiment 37, the process is configured according to any its embodiments 30 to 36, wherein in at least one of the multitudes of linear sweeps the spot of the at least one processing beam sweeps across each position on the surface of the section at least once. Hence, in this embodiment, the respective multitude of linear sweeps covers the entire surface of the section. In other words, in this multitude of linear sweeps, the at least one processing beam scans the entire surface of the respective section.

In its embodiment 38, the process is configured according to its embodiment 37, wherein the linear sweeps of the at least one multitude of linear sweeps is repeated 1 to 15 times, in one embodiment 1 to 10 times, in one embodiment 1 to 8 times, in one embodiment 2 to 7 times, and in one embodiment 2 to 5 times.

In its embodiment 39, the process is configured according to any its preceding embodiments, wherein the process step b) does not include cutting the filament.

In its embodiment 40, the process is configured according to any its preceding embodiments, wherein, after the step b) the process further comprises a step of rolling up the multitude of segments of the filament on a take-up reel.

In its embodiment 41, the process is configured according to any its preceding embodiments, wherein, in the process step a), the filament is provided on a feed reel.

In its embodiment 42, the process is configured according to any its preceding embodiments, wherein the process is performed as a reel-to-reel-process.

In its embodiment 43, the process is configured according to any its preceding embodiments, wherein each of the segments of the multitude of segments has a length in the range from 50 μm to 10 mm, in one embodiment from 100 μm to 10 mm, in one embodiment from 1 to 10 mm, and in one embodiment from 1 to 8 mm.

A contribution to the solution of at least one of the above objects is provided by an embodiment 1 of a processed filament, according to one embodiment, obtainable by the process according to any of its embodiments.

In its embodiment 2, the processed filament is configured according to its embodiment 1, wherein the processed filament comprises the multitude of segments, wherein in the sections of the segments of the multitude of segments a] a thickness of the second layer is less than outside the sections, or b] the second layer has been removed.

In one embodiment, in the segments of the multitude of segments, the thickness of the second layer is, circumferentially around the processed filament, less than outside the segments. Further preferred, the second layer has been removed from circumferentially around the segments of the multitude of segments.

A contribution to the solution of at least one of the above objects is provided by an embodiment 1 of a filament, according to one embodiment, wherein the filament comprises a. a core, including a first metal, b. a first layer which
   i. is superimposed on the core, and
   ii. comprises a polymer, and c. a second layer which
   i. is superimposed on the first layer, and
   ii. comprises a second metal;

wherein the filament comprises p segments which follow one another in a longitudinal direction of the filament;

wherein the p segments are numbered from 1 to p in the longitudinal direction; wherein each of the p segments comprises p sections which are disposed circumferentially around the filament; wherein p is an integer which is at least 3; wherein for each integer k in the range from 1 to p the $k^{th}$ segment comprises exactly (p–[k–1]) sections which have been processed; wherein in each section that has been processed a] a thickness of the second layer is less than outside the sections which have been processed, or b] the second layer has been removed.

In its embodiment 2, the filament is configured according to its embodiment 1, wherein the filament is obtainable by the process according to any of its embodiments. In one embodiment, the filament is the processed filament as defined in the context of the process.

In its respective embodiment 3, the processed filament and the filament is configured according to its embodiment 1 or 2, wherein the processed filament, respectively the filament has a length in range from 10 m to 10 km, in one embodiment from 100 to 8 km, and in one embodiment from 500 m to 5 km.

In its respective embodiment 4, the processed filament and the filament is configured according to any of its embodiments 1 to 3, wherein the processed filament, respectively the filament is at least partially rolled up on a reel.

In its respective embodiment 5, the processed filament and the filament is configured according to its embodiment 1 or 2, wherein the processed filament, respectively the filament has a length in range from 0.5 to 5 cm, in one embodiment from 1 to 4 cm, and in one embodiment from 1 to 3 cm.

In its respective embodiment 6, the processed filament and the filament is configured according to any of its embodiments 1 to 5, wherein each of the segments has a length in the range from 50 µm to 10 mm, in one embodiment from 100 µm to 10 mm, in one embodiment from 1 to 10 mm, and in one embodiment from 1 to 8 mm.

In its respective embodiment 7, the processed filament and the filament is configured according to any of its embodiments 1 to 6, wherein outside the sections of the segments a thickness of the second layer is in a range from 1 to 25 µm, in one embodiment from 2 to 20 µm, in one embodiment from 3 to 17 µm, and in one embodiment from 5 to 15 µm. In one embodiment, in regions of the filament which have not been processed, the second layer has a thickness in one of the preceding ranges.

A contribution to the solution of at least one of the above objects is provided by an embodiment 1 of an electrical device, according to one embodiment, including at least a part of the processed filament or the filament, in each case according to any of its embodiments.

In its embodiment 2, the electrical device is configured according to its embodiment 1, wherein the electrical device comprises a sensor, which comprises the at least part of the processed filament. A preferred sensor is an electrochemical sensor.

In its embodiment 3, the electrical device is configured according to its embodiment 1 or 2, wherein the electrical device is a medical device. A preferred medical device is an implantable medical device.

A contribution to the solution of at least one of the above objects is provided by an embodiment 1 of a device 1, according to one embodiment, for preparing a processed filament in a process stream, the device including, as components, a) a first processing beam source, which designed and arranged to emit a first processing beam onto a first segment of a filament for processing the filament by interaction of the first processing beam with the first segment; and b) a further processing beam source, which designed and arranged to emit a further processing beam onto a further segment of the filament for processing the filament by interaction of the further processing beam with the further segment;

wherein the first segment and the further segment follow one another in a longitudinal direction of the filament. In one embodiment, the further processing beam source is disposed down-stream of the first processing beam source. In one embodiment, the device comprises at least 3, in one embodiment at least 4, and in one embodiment exactly 4, processing beam sources, wherein each of these processing beam sources is designed and arranged to emit a processing beam onto another segment of the filament for processing the filament by interaction of the respective processing beam with the respective segment. In one embodiment, all the processing beam sources are disposed one after the other in a direction of the process stream. A preferred processing beam source is a laser.

In its embodiment 2, the device 1 is configured according to its embodiment 1, wherein the first processing beam source is designed and arranged to emit the first processing beam onto a first section of the first segment of the filament for processing the filament by interaction of the first processing beam with the first section of the first segment, wherein the further processing beam source is designed and arranged to emit the further processing beam onto a further section of the further segment of the filament for processing the filament by interaction of the further processing beam with the further section of the further segment, wherein the first section and the further section are at different circumferential locations around the filament. In one embodiment, the device comprises at least 3, in one embodiment at least 4, and in one embodiment exactly 4, processing beam sources, wherein each processing beam source is designed and arranged to emit a processing beam onto a section of another segment of the filament for processing the filament by interaction of the respective processing beam with the respective section of respective segment, wherein the preceding sections are at different circumferential locations around the filament.

In its embodiment 3, the device 1 is configured according to its embodiment 1 or 2, wherein first processing beam source and the further processing beam source are designed and arranged for processing the filament by interaction of the first processing beam with the first section and of the further processing with the further section at least in temporal overlap with, in one embodiment simultaneously to, one another. In case of more than 2 processing beam sources, it is preferred that all the processing beam sources are designed and arranged for processing the filament by interaction of the processing beams from the processing beam sources with the respective sections at least in temporal overlap with, in one embodiment simultaneously to, one another.

In its embodiment 4, the device 1 is configured according to any of its embodiments 1 to 3, wherein the device is designed and arranged for conducting the process according to any of its embodiments.

In its embodiment 5, the device 1 is configured according to its embodiment 4, wherein the device comprises the filament.

In its embodiment 6, the device 1 is configured according to its embodiment 4 or 5, wherein the device comprises n processing beam sources, or m processing beam sources, or each of both, wherein each of the processing beam sources is designed and arranged to emit a processing beam onto a different segment of the filament for processing the filament by interaction of the processing beam with this segment, wherein the different segments follow one another in the longitudinal direction of the filament.

In its embodiment 7, the device 1 is configured according to its embodiment 6, wherein each of the processing beam sources is designed and arranged to emit its processing beam onto a section of the respective segment of the different segments of the filament for processing the filament by interaction of the processing beam with this section, wherein each of the sections is at a different circumferential location around the filament.

In its embodiment 8, the device 1 is configured according to any of its preceding embodiments, wherein the first processing beam source is a first electromagnetic emitter, or a first particle emitter, or both, wherein the further processing beam source is a further electromagnetic emitter, or a further particle emitter, or both.

In its embodiment 9, the device 1 is configured according to its embodiment 8, wherein the first electromagnetic emitter is a first laser and the first processing beam is a first laser beam, wherein the further electromagnetic emitter is a further laser and the further processing beam is a further laser beam. In one embodiment, the first laser beam or the further laser beam or each of both is one of the at least one laser beams of any of the embodiments 21 to 43 of the process according to one embodiment.

In its embodiment 10, the device 1 is configured according to its embodiment 9, wherein the first laser beam or the further laser beam or each of both has a spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm.

In its embodiment 11, the device 1 is configured according to its embodiment 9 or 10, wherein the first laser or the further laser of each of both is a solid-state laser. A gain medium of this solid-state laser is, in one embodiment, a crystal. A preferred crystal is doped with neodym. A preferred neodym-doped crystal comprises yttrium. A preferred crystal which comprises yttrium is selected from the group consisting of Nd:YAG, $Nd:Y_3Al_5$, $O_{12}$, and $Nd:YVO_4$. Therein, $Nd:YVO_4$ is preferred in one embodiment.

In its embodiment 12, the device 1 is configured according to any of its preceding embodiments, wherein the device further comprises a first scanning element and a further scanning element, wherein the first scanning element is designed and arranged for sweeping the first processing beam across a surface of the first segment, in one embodiment of the first section, wherein the further scanning element is designed and arranged for sweeping the further processing beam across a surface of the further segment, in one embodiment of the further section.

In its embodiment 13, the device 1 is configured according to any of its preceding embodiments, wherein the filament comprises a. a core, including a first metal,
b. a first layer which
   i. is superimposed on the core, and
   ii. comprises a polymer, and
c. a second layer which
   i. is superimposed on the first layer, and
   ii. comprises a second metal.

In one embodiment, the filament is the filament described in any of the embodiments of the process according to one embodiment.

In its embodiment 14, the device 1 is configured according to its embodiment 13, wherein the first processing beam source is designed and arranged to remove the second layer at least partially from the first segment, in one embodiment from the first section, of the filament, wherein the further processing beam source is designed and arranged to remove the second layer at least partially from the further segment, in one embodiment from the further section, of the filament.

A contribution to the solution of at least one of the above objects is provided by an embodiment 1 of a device 2, according to one embodiment, for preparing a processed filament in a process stream, the device including as components a) a first processing beam source, and
b) a processing beam distribution element,
   wherein the first processing beam source is designed and arranged
     a. to provide a first processing beam via the processing beam distribution element onto a first segment of a filament for processing the filament by interaction of the first processing beam with the first segment, and
     b. to provide a further processing beam via the processing beam distribution element onto a further segment of the filament for processing the filament by interaction of the further processing beam with the further segment, wherein the first segment and the further segment are follow one another in a longitudinal direction of the filament. In one embodiment, the first processing beam source is designed and arranged o provide at least 3, in one embodiment at least 4, and in one embodiment exactly 4, processing beams, each via the processing beam distribution element onto another segment of the filament for processing the filament by interaction of the respective processing beam with the respective segment.

In its embodiment 2, the device 2 is configured according to its embodiment 1, wherein the first processing beam source is designed and arranged a] to provide the first processing beam via the processing beam distribution element onto a first section of the first segment of the filament for processing the filament by interaction of the first processing beam with the first section of the first segment, and b] to provide the further processing beam via the processing beam distribution element onto a further section of the further segment of the filament for processing the filament by interaction of the further processing beam with the further section of the further segment, wherein the first section and the further section are at different circumferential locations around the filament. In one embodiment, the first processing beam source is designed and arranged to provide at least 3, in one embodiment at least 4, and in one embodiment exactly 4, processing beams, each via the processing beam distribution element onto a section of another segment of the filament for processing the filament by interaction of the respective processing beam with the respective section of the respective segment, wherein the sections of the different segments are at different circumferential locations around the filament.

In its embodiment 3, the device 2 is configured according to its embodiment 1 or 2, wherein first processing beam source and the processing beam distribution element are designed and arranged for processing the filament by interaction of the first processing beam with the first section and of the further processing with the further section at least in temporal overlap with, in one embodiment simultaneously to, one another. In case of more than 2 processing beams, the first processing beam source and the processing beam distribution element are, in one embodiment, designed and arranged for processing the filament by interaction of each processing beam with the respective section at least in temporal overlap with, in one embodiment simultaneously to, one another.

In its embodiment 4, the device 2 is configured according to any of its preceding embodiments, wherein the processing beam distribution element is arranged in a beam path between the first processing beam source and the filament.

In its embodiment 5, the device 2 is configured according to any of its preceding embodiments, wherein the processing beam distribution element is a beam splitter, which is designed and arranged to split a source beam which has been emitted by the first processing beam source into the first processing beam and the further processing beam.

In its embodiment 6, the device 2 is configured according to its embodiment 5, wherein the device further comprises a} a first scanning element, which is
    i} arranged in a beam path of the first processing beam between the processing beam distribution element and the filament, and
    ii} designed and arranged for sweeping the first processing beam across a surface of the first segment, in one embodiment of the first section; and
b} a further scanning element, which is
    i} arranged in a beam path of the further processing beam between the processing beam distribution element and the filament, and
    ii} designed and arranged for sweeping the further processing beam across a surface of the further segment, in one embodiment of the further section.

In its embodiment 7, the device 2 is configured according to any of its embodiments 1 to 4, wherein the processing beam distribution element is a scanning element, which is designed and arranged for sweeping the first processing beam across a surface of the first segment, in one embodiment of the first section, and for sweeping the further processing beam across a surface of the further segment, in one embodiment of the further section.

In its embodiment 8, the device 2 is configured according to its embodiment 7, wherein the device further comprises a beam splitter, which is arranged in a beam path between the processing beam distribution element and the filament, and is designed and arranged to split a source beam which has been emitted by the first processing beam source into the first processing beam and the further processing beam.

In its embodiment 9, the device 2 is configured according to any of its preceding embodiments, wherein the device is designed and arranged for conducting the process according to any of its embodiments.

In its embodiment 10, the device 2 is configured according to its embodiment 9, wherein the device comprises the filament.

In its embodiment 11, the device 2 is configured according to any of its preceding embodiments, wherein the first processing beam source is an electromagnetic emitter, or a particle emitter, or both.

In its embodiment 12, the device 2 is configured according to its embodiment 11, wherein the electromagnetic emitter is a laser, the first processing beam is a first laser beam, and the further processing beam is a further laser beam. In one embodiment, the first laser beam or the further laser beam or each of both is one of the at least one laser beams of any of the embodiments 21 to 43 of the process according to one embodiment.

In its embodiment 13, the device 2 is configured according to its embodiment 12, wherein the first laser beam or the further laser beam or each of both has a spectrum with a peak wavelength in the range from 430 to 780 nm, in one embodiment from 430 to 640 nm, in one embodiment from 430 to 600 nm, in one embodiment from 490 to 600 nm, in one embodiment from 490 to 570 nm, in one embodiment from 500 to 560 nm, in one embodiment from 510 to 550 nm, in one embodiment from 520 to 540 nm, in one embodiment from 525 to 540 nm, and in one embodiment from 528 to 536 nm.

In its embodiment 14, the device 2 is configured according to its embodiment 12 or 13, wherein the first laser or the further laser of each of both is a solid-state laser. A gain medium of this solid-state laser is, in one embodiment, a crystal. A preferred crystal is doped with neodym. A preferred neodym-doped crystal comprises yttrium. A preferred crystal which comprises yttrium is selected from the group consisting of $Nd:YAG$, $Nd:Y_3Al_5$, $O_{12}$, and $Nd:YVO_4$. Therein, $Nd:YVO_4$ is preferred in one embodiment.

In its embodiment 15, the device 2 is configured according to any of its preceding embodiments, wherein the filament comprises a. a core, including a first metal,
b. a first layer which
    i. is superimposed on the core, and
    ii. comprises a polymer, and
c. a second layer which
    i. is superimposed on the first layer, and
    ii. comprises a second metal.

In one embodiment, the filament is the filament described in any of the embodiments of the process according to one embodiment.

In its embodiment 16, the device 2 is configured according to its embodiment 15, wherein the first processing beam source is designed and arranged to remove the second layer at least partially from the first segment, in one embodiment from the first section, of the filament and at least partially from the further segment, in one embodiment from the further section, of the filament.

In its embodiment 15, the device 1 is configured according to any of its embodiments, in its embodiment 17, the device 2 is configured according to any of its embodiments, wherein, in each case, the device further comprises an imaging means, which designed and arranged to provide an image, in one embodiment a sequence of images, of the first segment or the further segment or each of both of the processed filament. Accordingly, the imaging means is, in one embodiment, arranged downstream, of the first processing beam source and in one embodiment also downstream of the further processing beam source. A preferred imaging means is an image capturing means. A preferred image capturing means is a camera. The image capturing means is designed and arranged for creating and recording an image, in one embodiment a sequence of images, of the first segment or the further segment or each of both of the processed filament.

In its embodiment 16, the device 1 is configured according to any of its embodiments, in its embodiment 18, the device 2 is configured according to any of its embodiments, wherein, in each case, the device is designed for a reel-to-reel-processing of the filament.

In its embodiment 17, the device 1 is configured according to any of its embodiments, in its embodiment 19, the device 2 is configured according to any of its embodiments, wherein, in each case, the device further comprises a guiding means, including a filament feed, which is arranged upstream of the first processing beam source, and designed to feed the filament from a feed reel. Here, the guiding means may include the feed reel or not.

In its embodiment 18, the device 1 is configured according to its embodiment 17, in its embodiment 20, the device 2 is configured according to its embodiment 19, wherein, in each case, the device comprises the feed reel.

In its embodiment 19, the device 1 is configured according to its embodiment 17 or 18, in its embodiment 21, the device 2 is configured according to its embodiment 19 or 20, wherein, in each case, the guiding means further comprises a filament take-up means, which is arranged down-stream of the first processing beam source, in one embodiment also down-stream of the further processing beam source. In one embodiment, between the filament feed and the filament take-up means, the device includes no means to cut the filament.

In its embodiment 20, the device 1 is configured according to its embodiment 19, in its embodiment 22, the device 2 is configured according to its embodiment 21, wherein, in each case, the filament take-up means is designed for the processed filament to be rolled up on a take-up reel. Here, the guiding means may include the take-up reel or not.

In its embodiment 21, the device 1 is configured according to its embodiment 20, in its embodiment 23, the device 2 is configured according to its embodiment 22, wherein, in each case, the device comprises the take-up reel.

In its embodiment 22, the device 1 is configured according to any of its embodiments 17 to 21, in its embodiment 24, the device 2 is configured according to any of its embodiments 19 to 23, wherein, in each case, the guiding means further comprises a first tension control means which is arranged up-stream of the first processing beam source, wherein the first tension control means is designed and arranged to adapt a tension of the first segment or of the further segment or of each of both during the processing. In one embodiment, the first tension control means is arranged between the filament feed and the first processing beam source.

In its embodiment 23, the device 1 is configured according to its embodiment 22, in its embodiment 25, the device 2 is configured according to its embodiment 24, wherein, in each case, the first tension control means comprises a first multitude of deflection rollers.

In its embodiment 24, the device 1 is configured according to any of its embodiments 17 to 23, in its embodiment 26, the device 2 is configured according to any of its embodiments 19 to 25, wherein, in each case, the guiding means further comprises a further tension control means which is arranged down-stream of the first processing beam source, in one embodiment also of the further processing beam source, wherein the further tension control means is designed and arranged to adapt a tension of the first segment or of the further segment or of each of both during the processing. In one embodiment, the further tension control means is arranged between the first processing beam source and the filament take-up means, in one embodiment between the further processing beam source and the filament take-up means.

In its embodiment 25, the device 1 is configured according to its embodiment 24, in its embodiment 27, the device 2 is configured according to its embodiment 26, wherein, in each case, the further tension control means comprises a further multitude of deflection rollers.

In its embodiment 26, the device 1 is configured according to any of its embodiments 18 to 25, in its embodiment 28, the device 2 is configured according to any of its embodiments 20 to 27, wherein, in each case, a first part of the filament is rolled up on the feed reel. The feed reel is, in one embodiment, arranged up-stream of the first processing beam source. In one embodiment, the first segment and the further segment are down-stream of the first part.

In its embodiment 27, the device 1 is configured according to any of its embodiments 21 to 26, in its embodiment 29, the device 2 is configured according to any of its embodiments 23 to 28, wherein, in each case, a further part of the filament is rolled up on the take-up reel. The take-up reel is, in one embodiment, arranged down-stream of the first processing beam source, in one embodiment also of the further processing beam source. In one embodiment, the first segment and the further segment are up-stream of the further part. Further preferred, the first segment and the further segment are between the first and the further part of the filament.

A contribution to the solution of at least one of the above objects is provided by an embodiment 1 of a use 1, according to one embodiment, of at least one laser for providing the at least one processing beam in one embodiment process according to any of its embodiments, or as the first processing beam source of the device 1 or 2, in each case according to any of its embodiments.

A contribution to the solution of at least one of the above objects is provided by an embodiment 1 of a use 2, according to one embodiment, of a filament for being processed in the process according to any of its embodiments, or by the device 1 or 2, in each case, according to any of its embodiments, in each case, thereby obtaining the processed filament from the filament. In one embodiment, the filament is the filament described in any of the embodiments of the process according to one embodiment.

Features described as preferred in one category of the embodiments, such as the process or the device 1 or 2, are likewise preferred in a respective embodiment of the further embodiments, including the processed filament and uses.

Filament

In the context of one embodiment, the filament may be any kind of filament which the skilled person deems appropriate. Herein, a filament is a linear, non-rigid element which has a length that is at least 10 times, in one embodiment at least 100 times, in one embodiment at least 1000 times, a diameter of the filament. Therein, "non-rigid" means that the filament is flexible at least to a degree which allows to reversibly roll the filament up on a roll without damaging the filament. In a cross-section which is perpendicular to the length of the filament, the filament may have any shape which the skilled person deems appropriate. In one embodiment, the filament has a cross-sectional shape, selected from the group consisting of circular, rectangular, oval, and elliptical, wherein a circular cross-section is preferred in one embodiment. In one embodiment, the filament has the preceding cross-sectional shape over its full length. A particularly preferred filament is a wire. The longitudinal direction of the filament is a direction of a length of the filament.
Segment Each segment of the multitude of segments is a longitudinally extending portion of the filament, wherein a length of the segment is shorter than the length of the filament. In one embodiment, the length of the filament is at least 100 times, in one embodiment at least 1000 times, the length of the segment. In one embodiment, the segments of the multitude of segments are spaced apart from one another in the longitudinal direction. This means that, in one embodiment, no 2 segments adjoin one another.
Structure of the Filament A preferred filament comprises a multilayer structure. The filament, in one embodiment, comprises the core, the first layer which superimpose the core and the second layer which superimposes the first layer. Herein, the term "superimpose" means that the entities given may follow one another directly, in case of which they are in contact with each other, or indirectly, in case of which there is at least one further entity in-between. Hence, there may or may not be further layers between the core and the first layer and/or the first layer and the second layer. In one embodiment, the first layer is in contact with the core. Additionally or alternatively preferred, the second layer is on contact with the first layer. In each cross-section through the filament, which is perpendicular to the length of the filament, the core, in one embodiment, comprises a geometric centre of the filament. Further, the second layer may be superimposed by a further layer on its outer side or not. In one embodiment, the second layer is not superimposed by any further layer on its outer side, i.e. the side which faces away from the core. Before processing the filament, the first layer, in one embodiment, superimposes the core over at least 50%, in one embodiment at least 60%, in one embodiment at least 70%, in one embodiment at least 80%, in one embodiment at least 90%, and in one embodiment 100%, in each case of an entire lateral surface of the core. Additionally or alternatively preferred, the second layer superimposes the first layer over at least 50%, in one embodiment at least 60%, in one embodiment at least 70%, in one embodiment at least 80%, in one embodiment at least 90%, and in one embodiment 100%, in each case of an entire lateral surface of the first layer, wherein this lateral surface faces away from the core. After processing the filament, the preceding holds, in one embodiment, outside of regions of the filament that have been processed. Hence, at least the sections which have been processed are excluded from this specification. The core, in one embodiment, is of a shape of a cylinder which may have been bend (oblique cylinder). In one embodiment, the first layer or the second layer or both is of the shape of a hollow cylinder, respectively. Herein, the term cylinder does not restrict a cross-sectional shape. A preferred cylinder is a circular cylinder (circular cross-sectional shape) or a prism (polygonal cross-sectional shape). The core, the first layer and the second layer may be co-axial or not. In particular, the second layer is often not co-axial to the core and the first layer.

The core of the filament comprises the first metal, in one embodiment, in a proportion in the range from 50 to 100 wt.-%, in one embodiment from 60 to 100 wt.-%, in one embodiment from 70 to 100 wt.-%, in one embodiment from 80 to 100 wt.-%, and in one embodiment from 90 to 100 wt.-%, in each case based on the weight of the core. A preferred first metal is biocompatible. In one embodiment, the overall core material is biocompatible. The first layer comprises the polymer, in one embodiment, in a proportion in the range from 50 to 100 wt.-%, in one embodiment from 60 to 100 wt.-%, in one embodiment from 70 to 100 wt. %, in one embodiment from 80 to 100 wt.-%, and in one embodiment from 90 to 100 wt.-%, in each case based on the weight of the first layer. In one embodiment, the polymer of the first layer, in one embodiment the overall material of the first layer is biocompatible. The second layer comprises the second metal, in one embodiment, in a proportion in the range from 50 to 100 wt.-%, in one embodiment from 60 to 100 wt.-%, in one embodiment from 70 to 100 wt. %, in one embodiment from 80 to 100 wt.-%, and in one embodiment from 90 to 100 wt.-%, in each case based on the weight of the second layer. In one embodiment, the second metal, in one embodiment the overall material of the second layer is biocompatible. In one embodiment, each of the materials of the filament defined herein is biocompatible. A preferred filament consists essentially of biocompatible materials. A preferred biocompatible material is one selected from the group consisting of biotolerant, bioinert and bioactive or a combination of at least two thereof. In one embodiment, the first metal or the second metal or each of both is a noble metal. In one embodiment, the first and second metals are different noble metals.

In a preferred filament, a surface of the first layer is characterised by an average roughness $R_a$ in the range from 0.07 to 4 μm, in one embodiment from 0.1 to 2 μm, in one embodiment from 0.2 to 1.2 μm; or by a root-mean-squared roughness $R_q$ in the range from 0.2 to 7 μm, in one embodiment from 0.5 to 4 μm, in one embodiment from 1 to 3.5 μm; or by each of both kinds of roughness. The preceding surface of the first layer, in one embodiment, faces the second layer. This means that the surface is, in one embodiment, an outer surface of the first layer. In one embodiment, the surface is at least part of a lateral surface of the first layer. In one embodiment, the surface represents 50 to 100%, in one embodiment 60 to 100%, in one embodiment 70 to 100%, in one embodiment 80 to 100%, in one embodiment 90 to 100%, and in one embodiment 95 to 100%, of an overall outer lateral surface of the first layer. In one embodiment, a surface of the core is characterised by an average roughness which is less, in one embodiment at least by a factor 0.1, than the average roughness $R_a$ of the surface of the first layer; or by a root-mean-squared roughness which is less, in one embodiment at least by a factor 0.1, than the root-mean-squared roughness $R_q$ of the surface of the first layer; or by both of the preceding specifications. In one embodiment, the average roughness of the surface of the core is in the range from 0.001 to 0.1 μm, in one embodiment from 0.005 to 0.05 μm, in one embodiment from 0.01 to 0.05 μm. Additionally or alternatively preferred, the root-mean-squared roughness of the surface of the core is in the range from 0.001 to 0.1 μm, in one embodiment from 0.006 to 0.06 μm, in one embodiment from 0.02 to 0.06 μm. The preceding surface of the core is, in one embodiment, at least part of a lateral surface of the core. In one embodiment, the surface represents 50 to 100%, in one embodiment 60 to 100%, in one embodiment 70 to 100%, in one embodiment 80 to 100%, in one embodiment 90 to 100%, and in one embodiment 95 to 100%, of an overall lateral surface of the core.
Guiding Means In the context of one embodiment, the guiding means may be any means which the skilled person deems suitable for guiding the filament such that the segment is arranged during the processing in a predetermined orientation. In general, the guiding means is one or more elements of the device 1 or 2 according to one embodiment which defines an orientation of a the segment during processing this segment.

Further, the guiding means may define a fixation of the segment during processing or a tension of the segment during processing or both. The orientation of the segment may, for example, be achieved by an appropriate arrangement of the filament feed or the filament take-up means or both. Alternatively, the orientation of the segment during processing may be achieved by means of suitably arranged deflection rollers of the guiding means. Those deflection rollers may be part of the first and/or further tension control means.

Processing

In the context of one embodiment, the processing of the filament may be any kind of processing which the skilled person deems appropriate and which can be achieved by interaction of the at least one processing beam with the section or segment of the filament. A preferred interaction is absorption. A particularly preferred processing includes removing part of the filament in the section or segment, in one embodiment by ablation, in one embodiment laser-ablation.

Reel-to-Reel-Processing

Reel-to-reel-processing means provision of the filament at least partially rolled up on a reel, at least partially unwinding the filament from the reel, then processing and then at least partially re-winding the processed filament on a further reel. In one embodiment, the filament is not cut in that process. Here, cutting means separating the filament into at least two distinct filaments.

Diameter

In case of a non-circular shape, such as a cross-section of the filament, the diameter of the shape is a length of a longest straight line which starts and ends on the edge of the shape.

Scanning Element

In the context of one embodiment, the recited scanning elements may be any element which the skilled person deems suitable for sweeping the respective processing beam across a surface of the respective segment or section. By means of the scanning element, the processing beam can be provided to different target locations one after the other, but not simultaneously to the different target locations. The latter requires to split up the beam which can be done by a beam splitter. The scanning element is, in one embodiment, an optical component which is designed to deflect a processing beam, in one embodiment a laser beam. Therein, an angle of deflection can, in one embodiment, be changed, in one embodiment scanned across an angular range. A preferred scanning element comprises a mirror which is designed and arranged in a movable manner. In one embodiment the mirror can be swiveled around an axis of rotation. A preferred scanning element is of a galvanometer type.

Test Methods

The test methods which follow were utilized within the context of one embodiment. Unless stated otherwise, the measurements were conducted at an ambient temperature of 23° C., an ambient air pressure of 100 kPa (0.986 atm) and a relative air humidity of 50%.

Average Roughness $R_a$ and Root-Mean-Squared Roughness $R_q$

In order to determine the roughness of a surface of layer or of the core of the filament, a cross-section through the filament which is perpendicular to the filament length is prepared. The cross-section is polished prior to focussed-ion-beam (FIB) inspection. An FIB image is assessed using suitable image editing software. Depending on the general cross-sectional shape of the surface to be examined, a suitable geometric form is drawn. In the case of a circular filament, a circle is drawn. The diameter of the circle is chosen to match the diameter of the surface to be examined in the cross-section. The position of the circle is fitted to the surface to be examined. The distance of the surface to the circle in radial direction is measured at 10 positions equidistantly around the circumference of the circle (see FIG. 19). The average roughness $R_a$ is obtained by calculating the arithmetic mean of the 10 distances, whereas the rootmean-squared roughness $R_q$ is obtained by calculating the root mean square of the 10 distances.

Spectrum and Peak Wavelength

In case of a laser beam as processing beam, the peak wavelength of the spectrum is the nominal peak wavelength of the laser output. This is either the wavelength at which the laser lases or, if a non-linear optical process is used to alter the output wavelength, the respective harmonic of the lasing wavelength. For example, a KrF-Excimer laser typically has a lasing wavelength at about 248 nm. A Nd:YVO$_4$-laser typically has a lasing wavelength at about 1064 nm. If the light of the Nd:YVO$_4$-laser is frequency doubled, the peak wavelength of the laser output is at about 532 nm. If the processing beam is not a laser beam, but another type of beam of electromagnetic radiation, the spectrum of this electromagnetic radiation is measured using a spectrometer of the type CCS200 from Thorlabs GmbH. The measurement is conducted in accordance with the manufacturer's instructions. The peak wavelength of the measured spectrum is then a local maximum of the spectrum which is also its global maximum.

Pulse Frequency

The pulse Frequency is defined as the number of pulses, emitted per unit of time. The pulse frequency of a pulsed laser is adjusted at the device. Any pulse frequency, referred to herein, means the pulse frequency as adjusted at the device.

Pulse Duration

The pulse duration is defined as the time duration between the intensity levels of a pulse measured at FWHM (full width at half-maximum). It is measured with a suitable photo diode and an oscilloscope.

Fluence

The fluence is defined as energy per pulse [J]/effective focal spot area [cm$^2$]. Therein, the effective focal spot area is calculated as the area of a circle of a diameter which is the spot size according to the test method below.

Energy per Pulse

The energy per pulse is determined by first measuring the accumulated energy of the beam over a period of irradiation of 1 second using a thermal power meter. If the focus of the beam is on the workpiece, this energy is measured right in front of the workpiece, i.e. slightly out of the focus point. The pulse frequency is determined as described above. The energy per pulse is calculated by dividing the accumulated energy by the pulse frequency in Hz.

Spot Size

The 2D-intensity distribution of the spot is measured using a 2D power meter. The spot size is determined by fitting a circle to the Full Width at half Maximum of the 2D-intensity distribution. The spot size is the diameter of this circle.

Aspects are illustrated further by way of example hereinafter by examples and figures. The embodiments are neither restricted to the examples nor the figures.

In the comparative examples (not according to the invention) and the examples (according to the invention), wires which have been prepared as described below are processed as described further below.

Preparation of Wires 3 km long wires which consist from the inside to the outside of a core of tantalum, a platinum layer, a polyurethane layer and a layer consisting of a mixture of silver and AgCl (Ag/AgCl-layer), are prepared as described in the following.

A wire precursor consisting of a core of tantalum and a cladding of platinum is prepared. This is effected by drawing a tube made of platinum on a rod made of tantalum. Further a conventional wire drawing method is applied to the wire precursor. This includes single die drawing (elongation per die 5 to 15%) the wire precursor at a drawing speed of about 10 m/min using lubrication oil. Ultrasonic cleaning and rinsing of the wire precursor are conducted in-line. Subsequently, an intermediate annealing step is conducted at an annealing temperature of 800° C. Therein, the wire precursor is moved through a furnace at an annealing speed of 20 m/min. Thereby, mechanical properties of the wire precursor are adjusted. Subsequently, multi die drawing (elongation per die 10 to 20%) is conducted at a drawing speed of 30 m/min using lubrication oil. Ultrasonic cleaning and rinsing of the wire precursor are conducted in-line. Further in-line, the wire precursor is coated with a resin of polyurethane. This is done by applying a wet film of the resin on the wire using enameling dies. Then the applied resin is dried thermally and the polymer is cured in an annealer. The applying, drying and curing steps are repeated 10 to 40 times in order to obtained a polyurethane layer thickness of about 20 μm. The polyurethane layer is coated in-line with an Ag/AgCl-layer.

This is done by applying a paste, which includes silver particles, AgCl, binder and solvent, to the polyurethane layer by enamel dies. The applied paste is dried thermally and cured. The steps of applying, drying and curing are repeated 2 to 10 times in order to obtain a 10 μm thick Ag/AgCl. A paste with a fineness of grind (as defined in ASTM D1316) of about 12 to 5 μm (50 point) and about 12 to 20 μm (fourth continuous scratch), and a temperature of about 300 to 450° C. is used for application of the Ag/AgCl layer.

Fineness of grind as defined in ASTM D1316 is measured by dragging a paste through a wedge using a scraping tool, from the deep end to the shallow end, and the location of the fourth continuous scratch is measured at a scale. This value corresponds to the fourth-largest particle agglomerate size in the paste. Furthermore, the so-called "50 point" is measured at the location where half of the surface of the wedge is scratched.

Wire Processing

Example 1

In the example 1, wires which have been prepared as described above are processed in a reel-to-reel fashion. A setup in accordance with FIG. 14, however, with 4 instead of only 2 lasers as processing beam sources, is used. Each 25 mm of the wire, an about 7 mm long segment of the wire is processed by completely laser-ablating the Ag/AgCl-layer from circumferentially around the wire. Here, 4 Nd:YVO$_4$-lasers, each having a peak output wavelength at 532 nm, are used as processing beam sources. The preceding output wavelength is obtained by frequency doubling the lasing wavelength of about 1064 nm of the Nd:YVO$_4$-crystal. For the laser ablation, the laser is pulsed at a frequency of 160 kHz, wherein each pulse has an energy of 5 μJ and a duration (width) of about 60 ns. The laser beam is focussed down to a focal beam diameter of 15 μm on the wire surface. Each laser pulse has a fluence of 2.8 J/cm$^2$.

The processing is conducted as described in the context of FIGS. 7 to 11d). Hence, m=n=4. The processing, however, does not stop after 4 processing steps. Instead, the processing is set forth by starting another 4 processing steps which are followed by further 4 processing steps and so forth. After each processing step, the wire is shifted by the distance between two neighbouring segments, i.e. by 25 mm. Hence, consecutive blocks of 4 processing steps overlap with one another in terms of the segments which are processed in these blocks. This way an overall continuous process is obtained which allows to completely ablate the Ag/AgCl-layer from segments each 25 mm of the wire over its entire length.

Figures 17A, 17B:
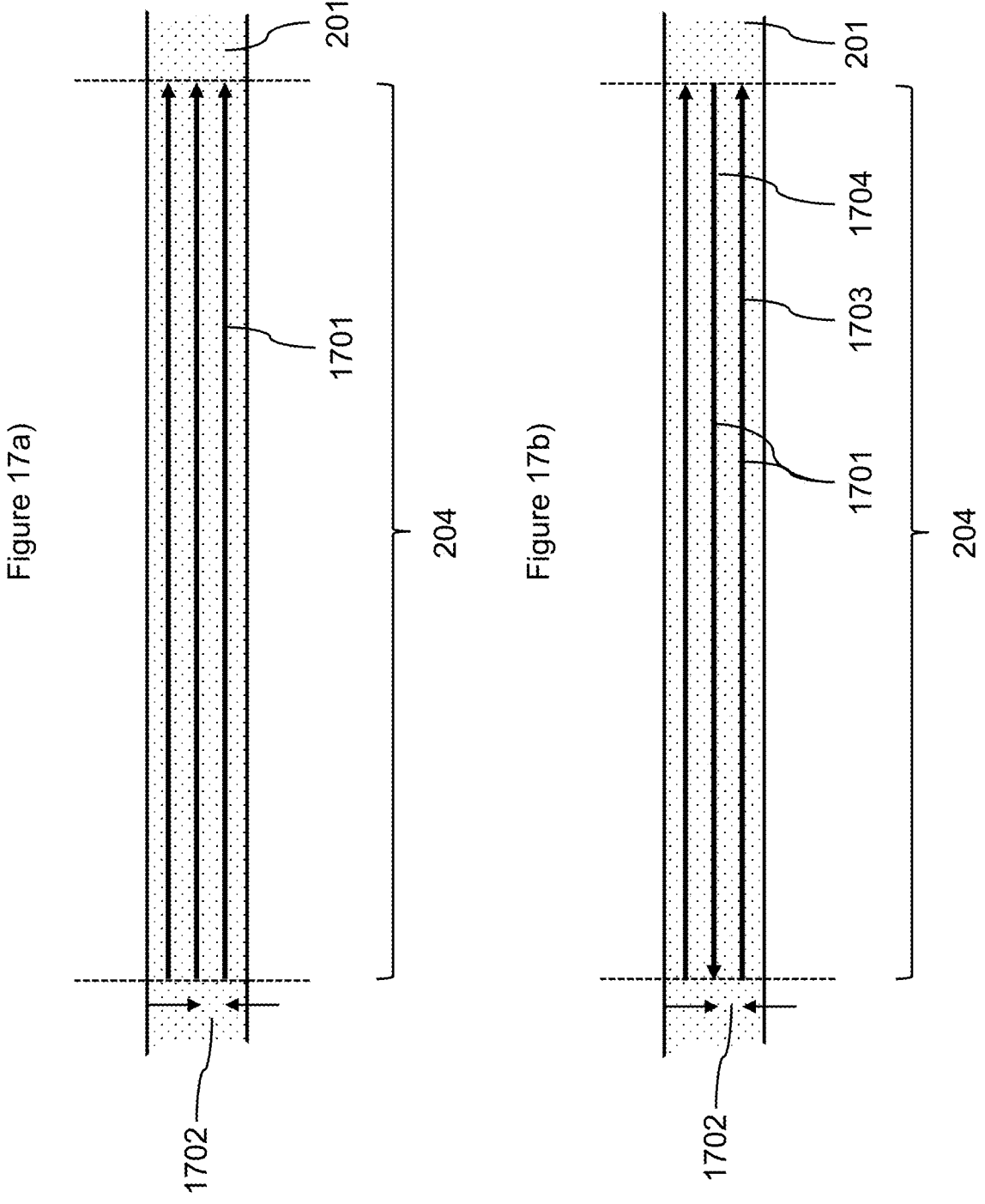
FIG. 17*a*) an illustration of parallel uni-directional processing.
FIG. 17*b*) an illustration of parallel bi-directional processing.

In the preceding, processing of each of the 4 sections of each segment is effected by scanning the laser focus over the respective section in form of a multitude of lines/sweeps as shown in FIG. 17a). The lines of each multitude are unidirectional and parallel to the length of the wire. Per section, this scanning is repeated 4 times, i.e. each section is scanned in 5 passes by the respective laser. Therein, the scanning speed of the laser is about 1250 mm/s. The distance between the lines/sweeps (pitch) is about 13 μm. In this particular example, the 4 sections of different segments which are processed in the same processing step are processed one after the other (sequentially).

Example 2

Example 2 is conducted as example 1, however, the processing of the 4 sections of different segments which are processed in the same processing step is conducted at the same time (simultaneously). Hence, the 4 lasers ablate at the same time in each of the processing steps.

Comparative Example 1

In the comparative example 1, the Ag/AgCl-layer is ablated in segments of the wire as described in example 1, except for the following differences. The 4 lasers are not positioned to provide their focal spots to 4 different longitudinal positions of the wire. Instead, all 4 lasers are arranged to irradiate the same longitudinal position (segment) of the wire, however, each at another circumferential region (section). Further, the processing is not conducted in accordance with the FIGS. 7 to 11d). Instead, the segments of the wire are processed one after the other. Hence, in each processing step, exactly 1 segment is ablated. This is effected, by activating the 4 lasers one after the other. Thus, in each of the process steps, first the first laser ablates the first section of the single segment to be processed in this process step, subsequently the second laser ablates the second section of the same segment, subsequently the third laser ablates the third section of the same segment, and subsequently the fourth laser ablates the fourth section of the same segment. This way the Ag/AgCl-layer is removed completely from the preceding segment. Subsequently, the wire is shifted by 25 mm and the next processing step is conducted at the next segment. In this particular, comparative example, a delay is incorporated between the consecutive laser ablation actions in the same processing step. The delay is selected to allow for sufficient dissipation of the heat introduced by the previous laser action in order not to overheat the wire and, thus, damage parts of the wire other than the Ag/AgCl-layer.

Comparative Example 2

Comparative example 2 is conducted as comparative example 1, however, without the delay between consecutive laser ablation actions in the same processing step. Instead, the ablation steps are conducted directly one after the other.

Comparative Example 3

Comparative example 3 is conducted as comparative example 1 with the following exception. In each of the processing steps, the 4 lasers ablate the Ag/AgCl-layer from the 4 sections of the same segment simultaneously. Hence, the Ag/AgCl-layer is removed from each segment by simultaneously irradiating the segment from all 4 sides circumferentially around the wire.

Evaluation

The above described methods of processing the wires are assessed in terms of their overall process step. i.e. in terms of the time which is needed to process the whole wire. After having processed the wires as described above for the comparative examples and examples, the processed segments of the wires are studied under an optical microscope for damages to the PU-layer which has been laid open. Any changes to the layer surface, such as molten regions or structures introduced to the surface of the PU-layer, are rated as disadvantageous. As a reference without damages to the PU-layer, a wire precursor which has been prepared as described above, but without application of the Ag/AgCl-layer is used.

The results of the above studies are summarised in the below table. Therein, "−−" means a result which is less favourable than "−", "−" means a result which is less favourable than "+", and "+" means a result which is less favourable than "++".

| | High Process Speed | Avoidance of Damages to the Wire |
|---|---|---|
| Comparative Example 1 | − | + |
| Comparative Example 2 | + | − |
| Comparative Example 3 | ++ | −− |
| Example 1 | + | + |
| Example 2 | ++ | + |

From the results of the comparative examples 1 to 3, it can be seen that there is a trade-off between high process speed, i.e. high production rate, and the goal to avoid damages to the PU-layer, i.e. a high quality of processed wires. Here, it should be considered that damaging the PU-layer means to partially structure the outer surface of the PU-layer. In result, a surface tension of the outer surface of the PU-layer is not uniform across the exposed region of the PU-layer. In preparing an electrochemical sensor, this may lead to non-uniform coating thicknesses of enzyme layers on the wire. The signal-to-noise ratio of the sensor as well as the linearity of the sensor response may suffer in result. Hence, in the technical field of the embodiments, the above trade-off is between high production rates and high accuracies of electrochemical sensors. This trade-off is resolved in the examples 1 and 2. Hence, the process according to one embodiment allows to produce wires for high accuracy electrochemical sensors at a high production rate.

Figures 2A, 2B:
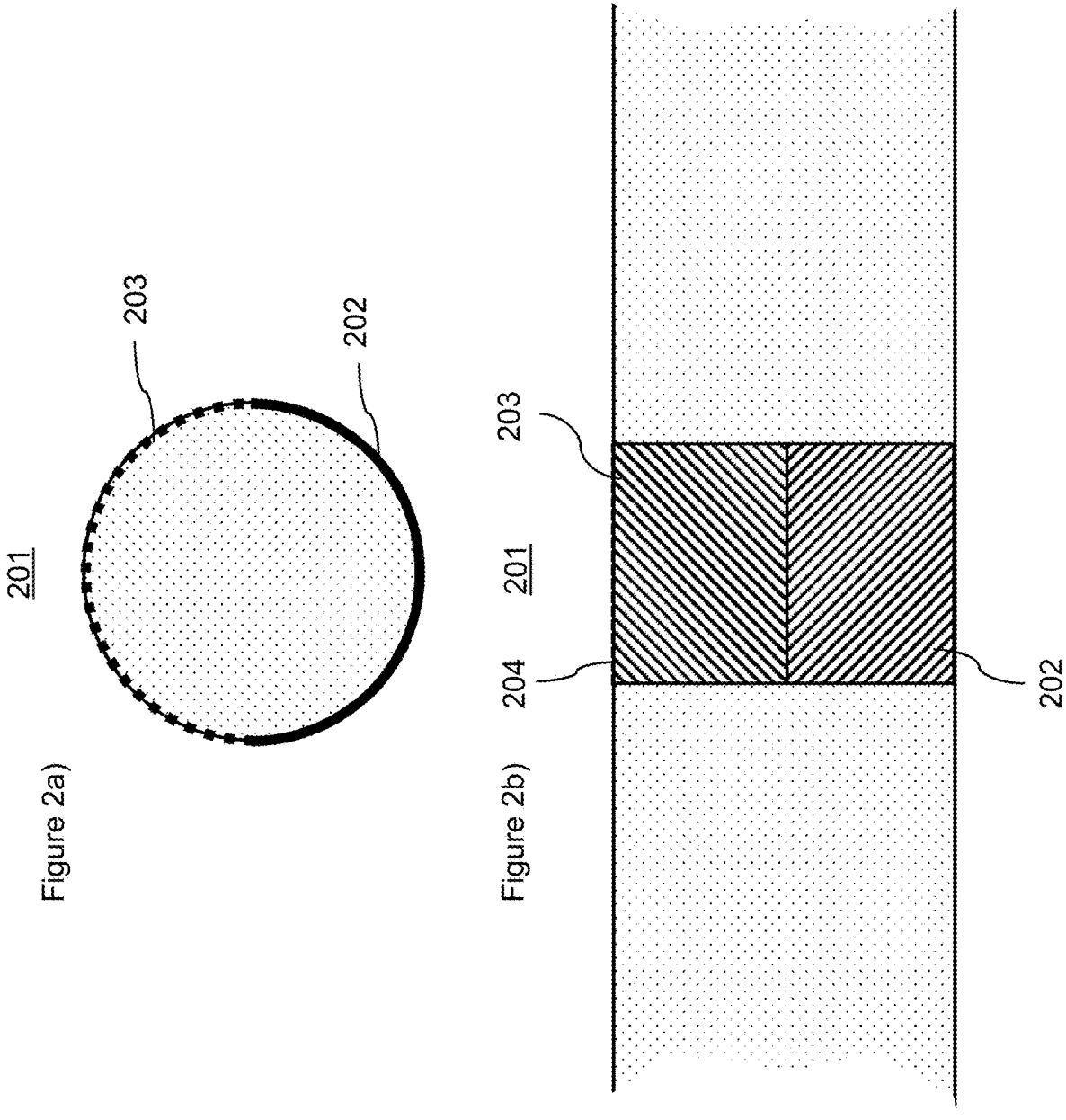
FIG. 2a) a cross-section through a filament to be processed by the process of FIG. 1, depicting the sections of a segment.
FIG. 2b) the filament of FIG. 2a) in side view.

FIG. 1 shows a flow-chart of a process 100 for preparing a processed filament 410 according to one embodiment. This process 100 comprises a process step a) 101 of providing a filament 201, which comprises a multitude of segments 204, which follow one another in a longitudinal direction 401 of the filament 201. Each of these segments 204 consists a first section 202 and a second section 203, which are disposed circumferentially around the filament 201. The preceding definitions are illustrated by FIGS. 2a) and 2b). In a process step b) 102, the filament 201 is processed in a first processing step 103 and a second processing step 104. Thereby the processed filament 410 is obtained. The processing steps 103, 104 are defined further in the context of FIGS. 3) to 6b).

FIG. 2a) shows a cross-section through a filament 201 to be processed by the process 100 of FIG. 1. The cross-section has been made through one of the segments 204 of the filament 201. Here, the first section 202 and the second section 203 of this segment 204 are depicted by a full and a dashed line, respectively.

FIG. 2b) shows the filament 201 of FIG. 2a) in side view.

Figure 3:
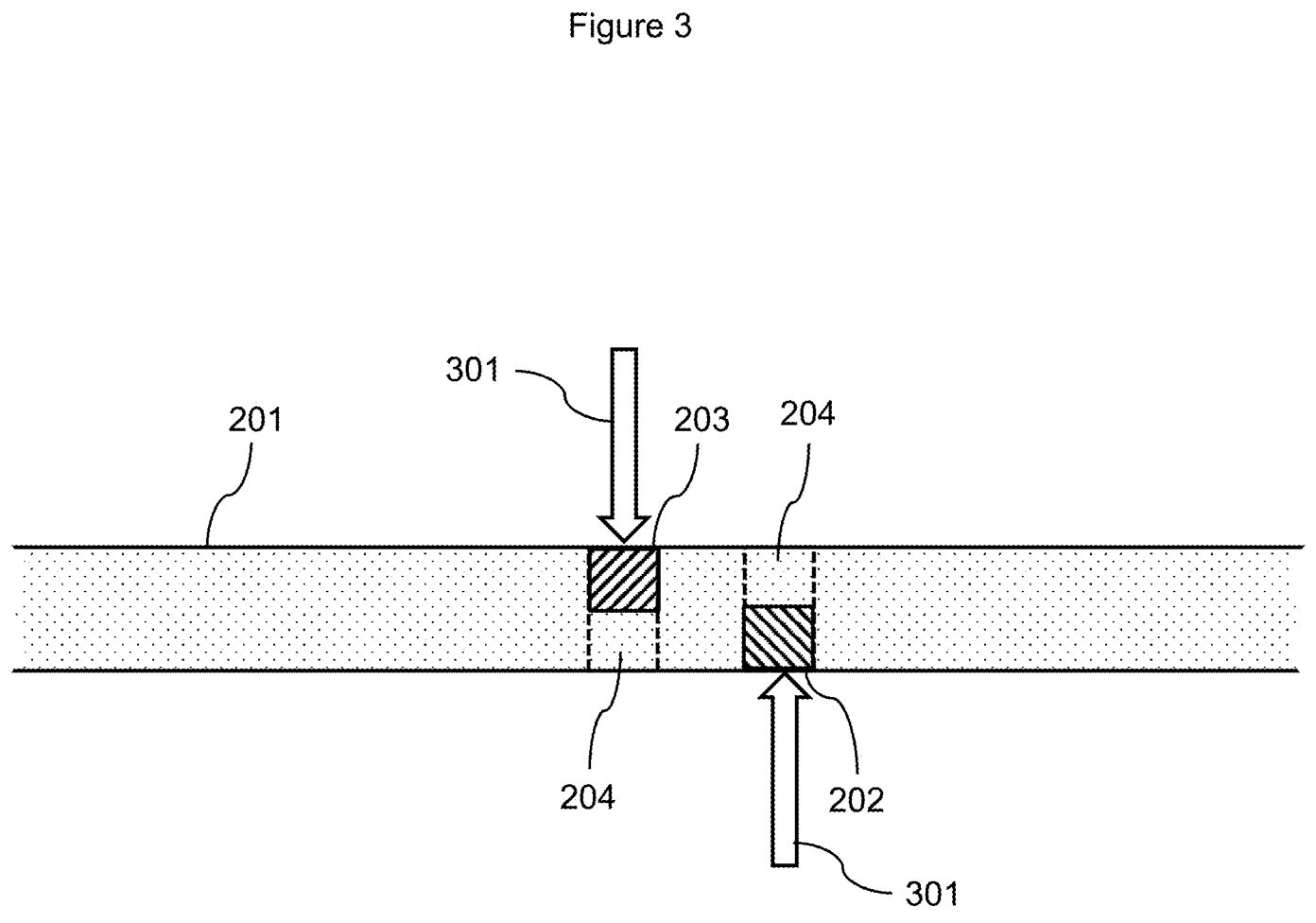

FIG. 3 shows a scheme for illustration of the processing steps 103, 104 of the process 100 of FIG. 1. What is shown is that each of the processing steps 103, 104 includes processing the second section 203 of one of the segments 204 and processing the first section 202 of a neighbouring segment 204, which follows the other segment 204 in the longitudinal direction 401 of the filament 201. Therein processing a section 202, 203 means irradiating this section 202, 203 with a processing beam 301 which is a laser beam for laser ablation.

Figures 4A, 4B:
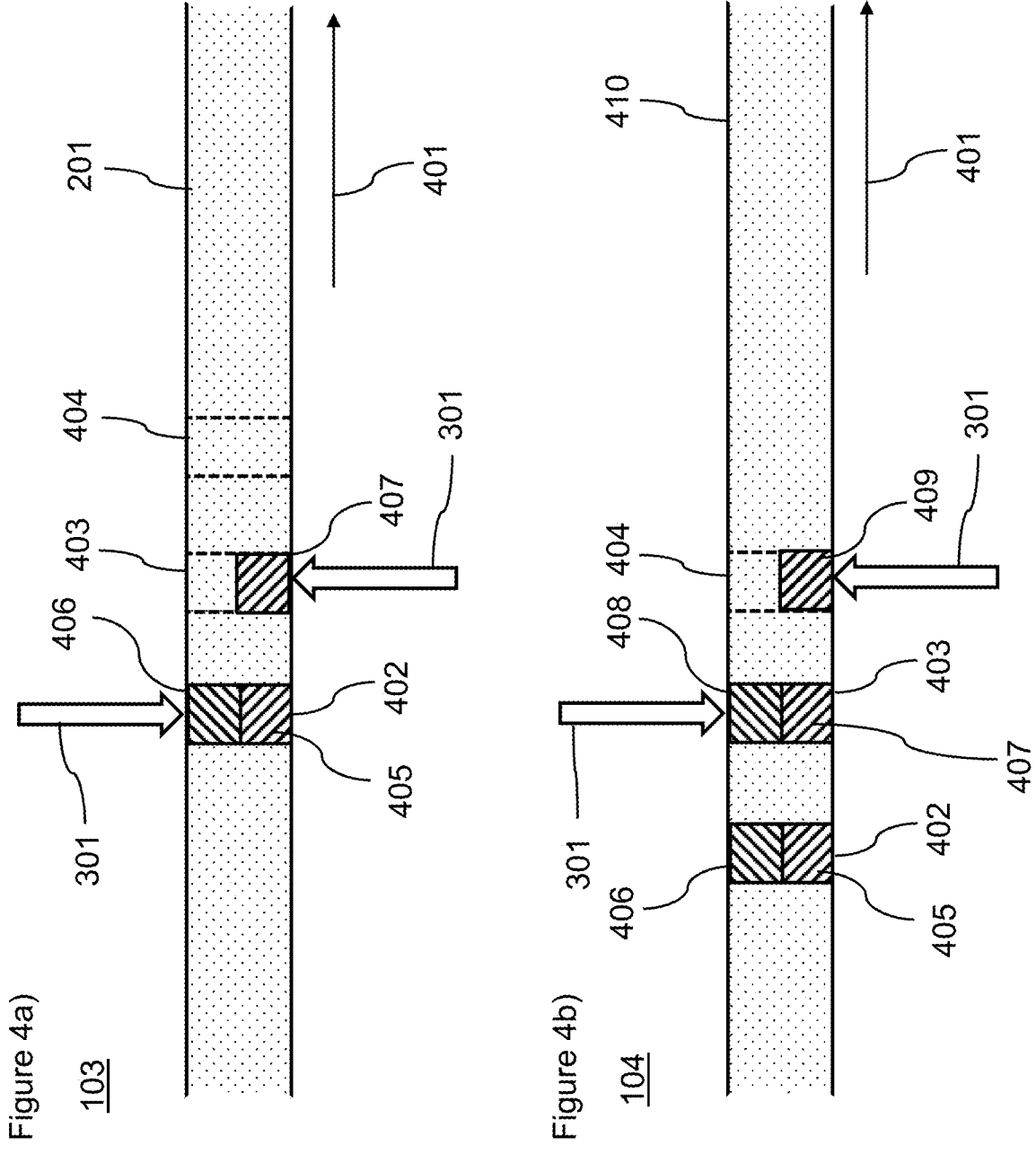
FIG. 4a) a scheme for illustration of the first processing step of the process of FIG. 1.
FIG. 4b) a scheme for illustration of the second processing step of the process of FIG. 1.

FIG. 4a) shows a scheme for illustration of the first processing step 103 of the process 100 of FIG. 1. What is shown is the filament 201 in a side view. A first segment 402, a second segment 403 and a third segment 404 of the filament 201 are depicted. Those segments follow one another equidistantly in the longitudinal direction 401. In the first processing step 103, a processing beam 301 processes a second section 406 of the first segment 402, whereas another processing beam 301 processes a first section 407 of the second segment 403. A first section 405 of the first segment 402 has already been processed before the first processing step 103. The third segment 404 is not processed in the first processing step 103.

FIG. 4b) shows scheme for illustration of the second processing step 104 of the process 100 of FIG. 1. Between the first 103 and second processing steps 104, the filament 201 has been shifted opposite to the longitudinal direction 401 by a distance between 2 neighbouring segments of the first through third segments 402 to 404. In the second processing step 104, a processing beam 301 processes a second section 408 of the second segment 403, whereas another processing beam 301 processes a first section 409 of the third segment 404. Thereby, the processed filament 410 is obtained.

Figure 5B:
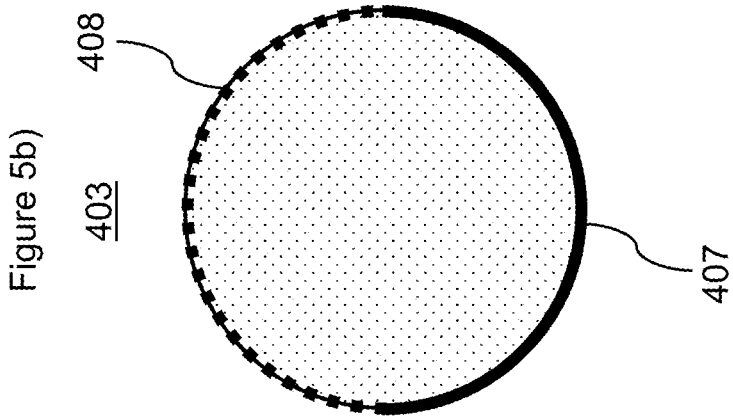
FIG. 5b) a cross-section through the second segment of the processed filament after the second processing step of the process of FIG. 1.
Figure 5A:
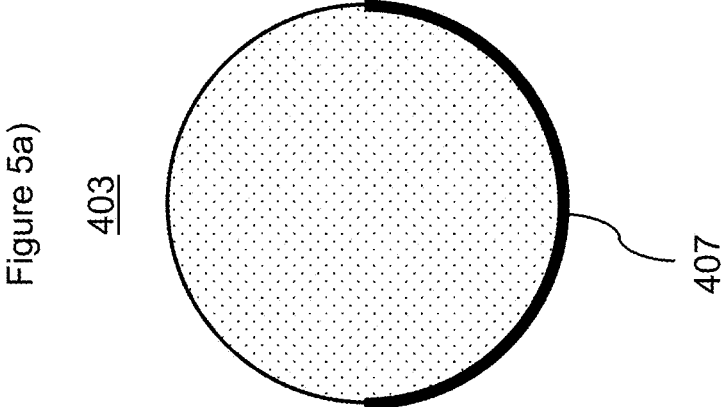
FIG. 5a) a cross-section through the second segment of the filament after the first processing step of the process of FIG. 1.

FIG. 5a) shows a cross-section through the second segment 403 of the filament 201 after the first processing step 103 of the process 100 of FIG. 1. In that situation, the first section 407 of the second segment 403 has just been processed. This is indicated by a full line which depicts the processed first section 407 in the figure.

FIG. 5b) shows a cross-section through the second segment 403 of the processed filament 410 after the second processing step 104 of the process 100 of FIG. 1. With respect to FIG. 5a), not only the first section 407 of the second segment 403, but also the second section 408 (dashed line) has been processed.

FIG. 6a) shows a side view of the second segment 403 of the filament 201 after the first processing step 103 of the process 100 of FIG. 1. FIG. 6a) shows the situation of FIG. 5a) in the side view.

FIG. 6b) shows a side view of the second segment 403 of the processed filament 410 after the second processing step 104 of the process 100 of FIG. 1. FIG. 6b) shows the situation of FIG. 5b) in the side view.

Figure 7:
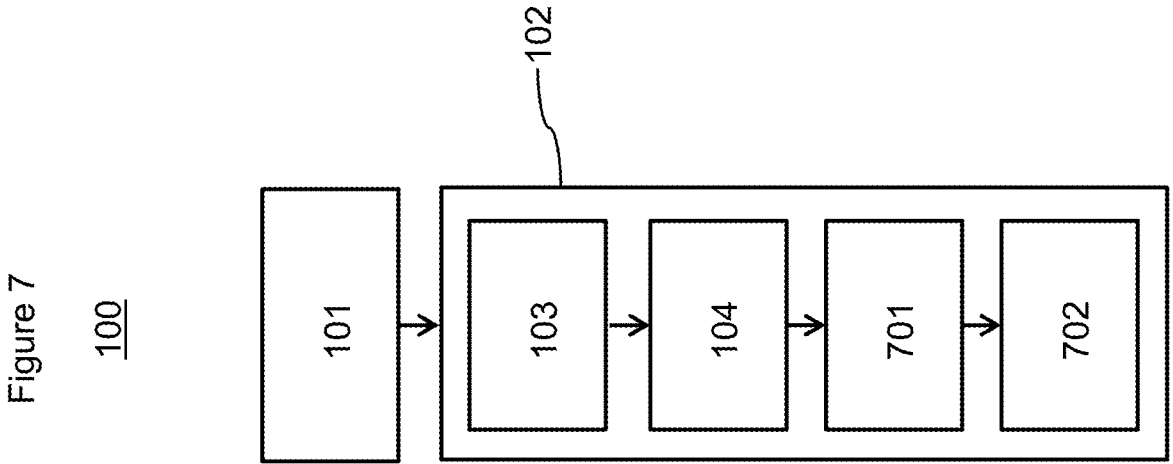
FIG. 7 a flow-chart of a further process according to one embodiment.
Figures 8A, 8B:
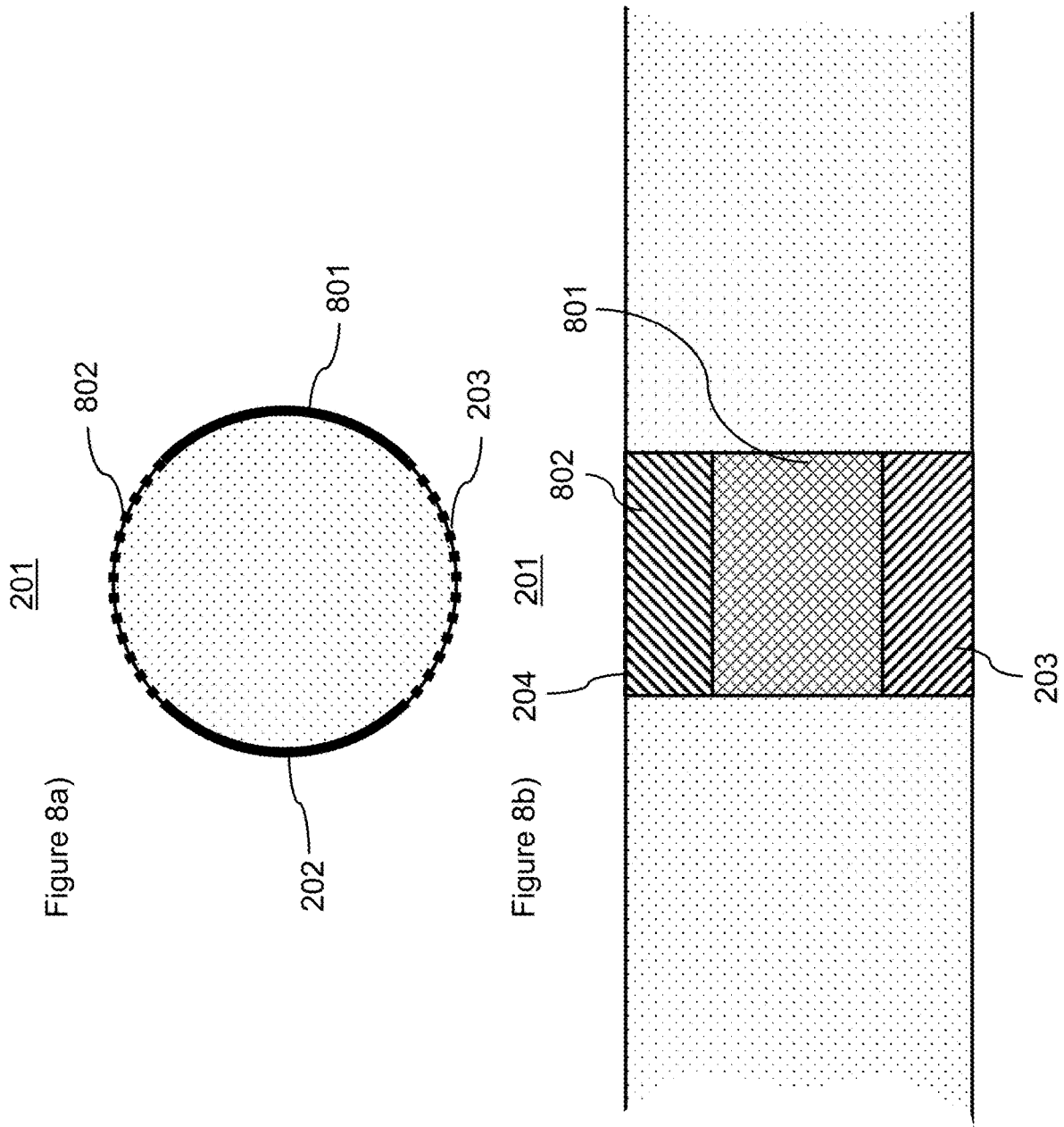
FIG. 8a) a cross-section through a filament to be processed by the process of FIG. 7, depicting the sections of a segment.
FIG. 8b) the filament of FIG. 8a) in side view.

FIG. 7 shows a flow-chart of a further process 100 for preparing a processed filament 410 according to one embodiment. This process 100 comprises a process step a) 101 of providing a filament 201, which comprises a multitude of segments 204, which follow one another equidistantly in a longitudinal direction 401 of the filament 201. Each of these segments 204 consists a first section 202, a second section 203, a third section 801 and a fourth section 802, which are disposed circumferentially around the filament 201. The preceding definitions are illustrated by FIGS. 8a) and 8b). In a process step b) 102, the filament 201 is processed in a sequence of first 103 through fourth processing steps 702. Thereby the processed filament 410 is obtained. The processing steps 103, 104 are defined further in the context of FIGS. 9 to 11d).

FIG. 8a) shows a cross-section through a filament 201 to be processed by the process 100 of FIG. 7. The cross-section has been made through one of the segments 204 of the filament 201. Here, the first section 202, the second section 203, the third section 801 and the fourth section 802 of this segment 204 are depicted by different lines.

FIG. 8b) shows the filament 201 of FIG. 8a) in side view. Here, the first section 202 cannot be seen as it is at the backside of the filament 201.

Figure 9:
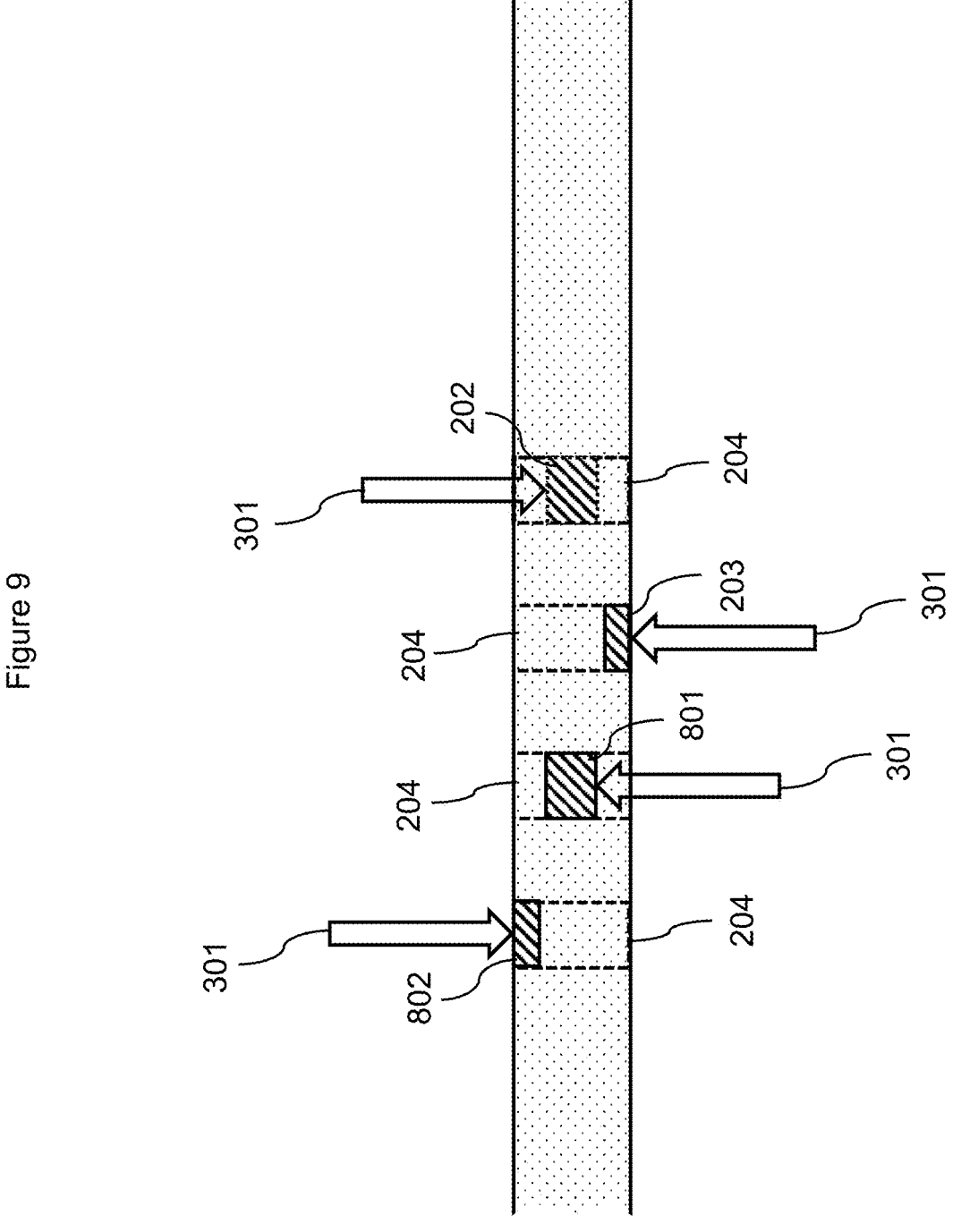
FIG. 9 a scheme for illustration of a general processing step of the process of FIG. 7.

FIG. 9 shows a scheme for illustration of the first 103 through fourth processing steps 702 of the process 100 of FIG. 1. What is shown is that each of the processing steps 103, 104, 701, 702 includes processing the fourth section 802 of one of the segments 204, processing the third section 801 of the next neighbouring segment 204, which follows the other segment 204 in the longitudinal direction 401 of the filament 201, processing the second section 203 of the next neighbouring segment 204 and processing the first section 202 (at the backside of the filament 201 in the figure) of the next neighbouring segment 204. Therein processing a section means irradiating this section with a processing beam 301 which is a laser beam for laser ablation. Between consecutive processing steps the filament is shifted in the longitudinal direction 401 (to the left in the figure) by a distance between neighbouring segments. The processing beams 301 are then provided at the same place in the reference space. This is similar to what is shown in FIGS. 4a) and 4b) for the two processing steps of the process of FIG. 1, but extended to 4 sections per segment and 4 processing steps.

FIG. 10a) shows a cross-section through the fourth segment 1000 of the filament 201 after the first processing step 103 of the process 100 of FIG. 7. In that situation, the first section 1001 of the fourth segment 1000 has just been processed. This is indicated by a full line which depicts the processed first section 1001 in the figure.

FIG. 10b) shows a cross-section through the 20fourth segment 1000 of the filament 201 after the second processing step 104 of the process 100 of FIG. 7. In that situation, the first section 1001 and the second section 1002 of the 20fourth segment 1000 have already been processed. This is indicated by the different bold lines in the figure.

FIG. 10c) shows a cross-section through the 20fourth segment 1000 of the filament 201 after the third processing step 701 of the process 100 of FIG. 7. In that situation, the first section 1001, the second section 1002 and the third section 1003 of the 20fourth segment 1000 have already been processed. This is indicated by the different bold lines in the figure.

FIG. 10d) shows a cross-section through the second segment of the processed filament 410 after the fourth processing step 702 of the process 100 of FIG. 7. In that situation, the first section 1001, the second section 1002, the third section 1003 and the fourth section 1004 of the 20fourth segment 1000 have already been processed. This is indicated by the different bold lines in the figure.

Figures 11A, 11B, 11C, 11D:
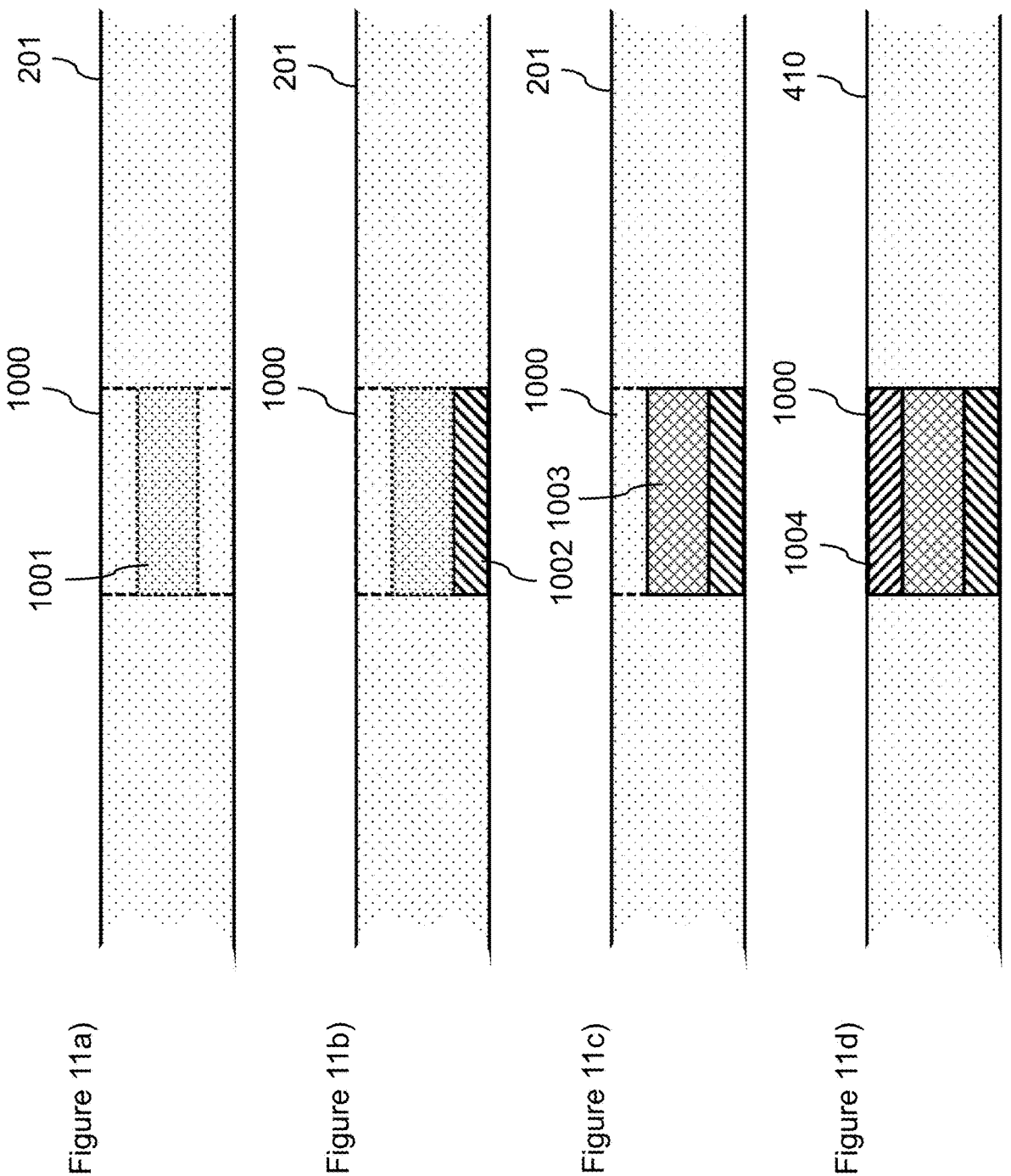
FIG. 11*a*) a side view of the fourth segment of the filament after the first processing step of the process of FIG. 7.
FIG. 11*b*) a side view of the fourth segment of the filament after the second processing step of the process of FIG. 7.
FIG. 11*c*) a side view of the fourth segment of the filament after the third processing step of the process of FIG. 7.
FIG. 11*d*) a side view of the fourth segment of the filament after the fourth processing step of the process of FIG. 7.

FIG. 11a) shows a side view of the 20fourth segment 1000 of the filament 201 after the first processing step 103 of the process 100 of FIG. 7. FIG. 11a) shows the situation of FIG. 10a) in the side view.

FIG. 11b) shows a side view of the 20fourth segment 1000 of the filament 201 after the second processing step 104 of the process 100 of FIG. 7. FIG. 11b) shows the situation of FIG. 10b) in the side view.

FIG. 11c) shows a side view of the 20fourth segment 1000 of the filament 201 after the third processing step 701 of the process 100 of FIG. 7. FIG. 11c) shows the situation of FIG. 10c) in the side view.

FIG. 11d) shows a side view of the 20fourth segment 1000 of the processed filament 410 after the fourth processing step 702 of the process 100 of FIG. 1. FIG. 11d) shows the situation of FIG. 10d) in the side view.

Figure 12:
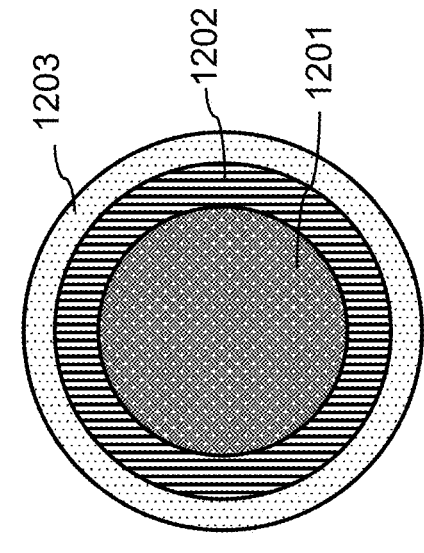
FIG. 12 a cross-section through a filament depicting the structure of the filament.

FIG. 12 shows a cross-section through the fourth segment 1000 of the filament 201 prior to the first processing step 103 of the process 100 of FIG. 7. A structure of the filament 201 is shown. As all the cross-sections of the figures, this one has been made with perpendicular orientation to a length of the filament 201. Over its entire length of 3 km, the filament 201 consists inside-out of a core 121, which is made from platinum; a first layer 1202, which is coated onto the core 1201 and made from a polyurethane; and a second layer 1203 which is coated onto the first layer 1202 and consists of a mixture of silver and AgCl. The filament 201 has an overall diameter of 200 µm. The filament 201 is a wire. Here, the core 1201, the first layer 1202 and the second layer 1203 are co-axial to one another.

Figure 13:
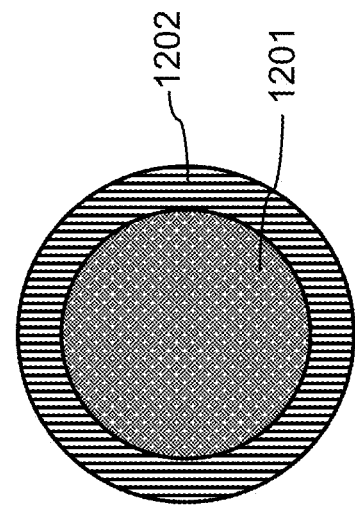
FIG. 13 a cross-section through a processed filament.

FIG. 13 shows a cross-section through the fourth segment 1000 of the processed filament 410 obtained in the fourth processing step 702 of the process 100 of FIG. 7. The cross-section has been made through the fourth segment 1000 of the processed filament 410 and with perpendicular orientation to a length of the processed filament 410. Comparison to FIG. 12 shows that the second layer 1203 has been completely ablated from circumferentially around the segment.

Figure 14:
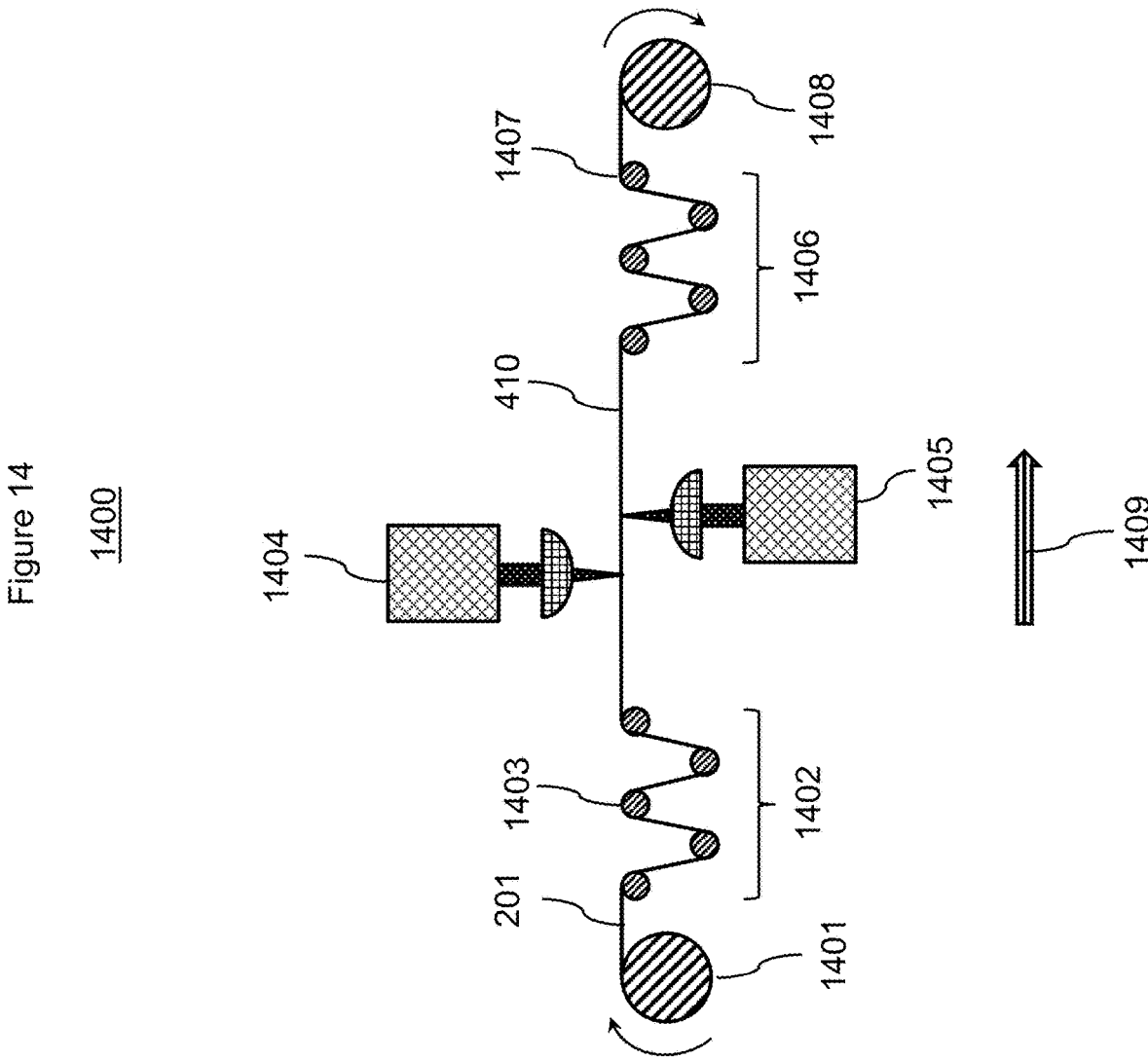
FIG. 14 a device according to one embodiment.

FIG. 14 shows a device 1400, according to one embodiment, for processing a filament 201 in a process stream 1409, thereby obtaining a processed filament 410. The device 1400 is configured for carrying out the process 100 of FIG. 1. The device 1400 comprises a first processing beam source 1404, which designed and arranged to emit a first processing beam onto a first section of a first segment of the filament 201 for processing the filament 201 by interaction of the first processing beam with the first section of the first segment. Down-stream of the first processing beam source 1404, the device 1400 comprises a further processing beam source 1405, which designed and arranged to emit a further processing beam onto a further section of a further segment of the filament 201 for processing the filament 201 by interaction of the further processing beam with the further section of the further segment. Therein, the first segment and the further segment follow one another in a longitudinal direction 401 of the filament 201, and the first section and the further section are at different circumferential locations around the filament 201. The first and further processing beam sources 1404, 1405 are frequency-doubled Nd:YVO₄-lasers. The device 1400 is designed for a reel-to-reel-processing of the filament 201. Accordingly, the device comprises a guiding means which, upstream of the laser, comprises a filament feed that is designed to feed the filament 201 from a feed reel 1401 which is also part of the device 1400. Further, downstream of the lasers, the guiding means comprises a filament take-up means which is designed for the processed filament 410 to be rolled up on a take-up reel 1408. Here, the guiding means includes the take-up reel 1408. The guiding means further comprises a first tension control means 14002 which is designed and arranged to adapt a tension of the first an further segments of the filament 201 during the processing. The first tension control means 1402 comprises a first multitude of deflection rollers 1403. In addition, the guiding means includes a further tension control means 1406 which is arranged downstream of the lasers. The further tension control means 1406, as well, is designed and arranged to adapt a tension of the first and further segments of the filament 201 during the processing. The further tension control means 1406 comprises a further multitude of deflection rollers 1407.

Figure 15:
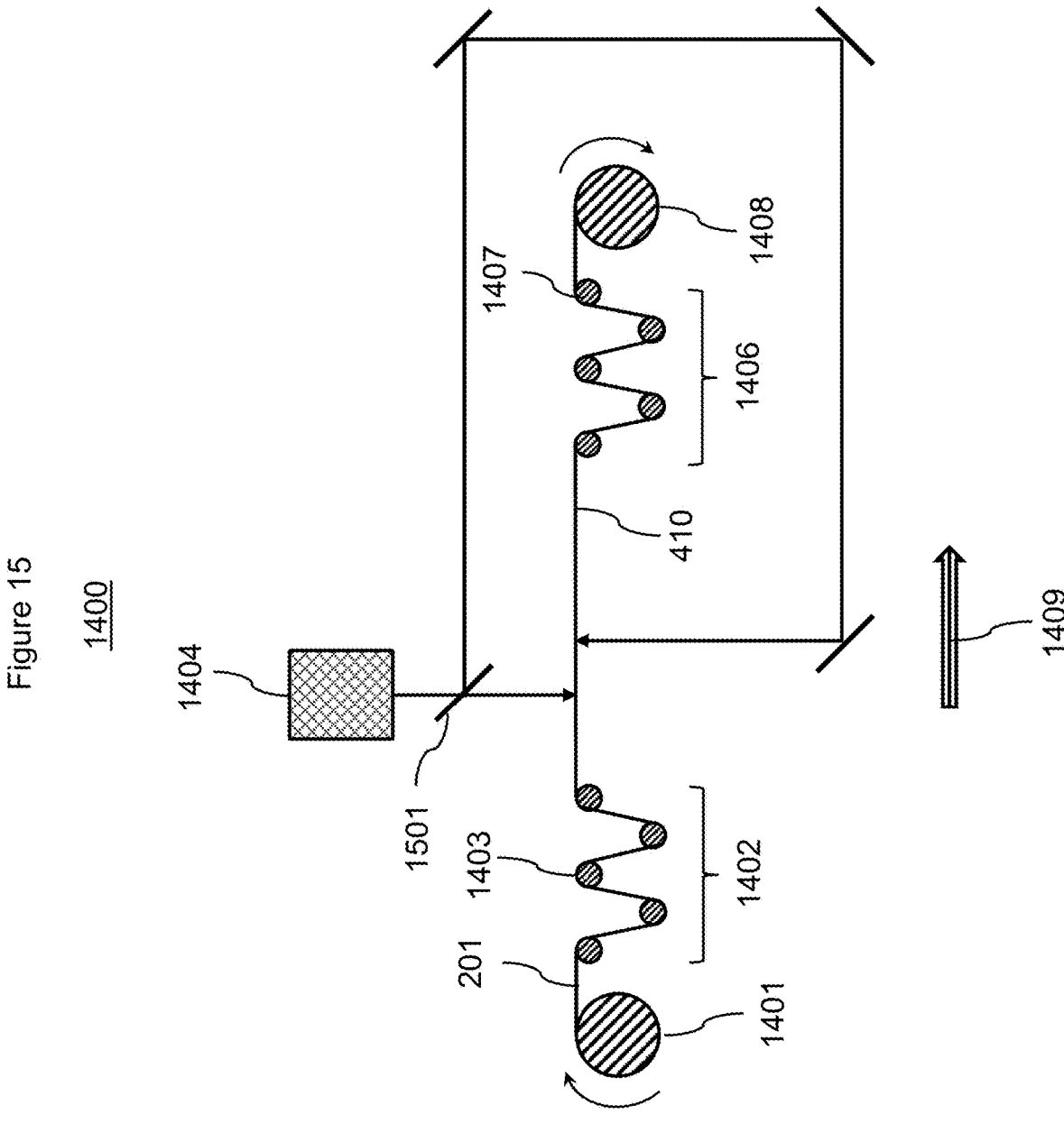
FIG. 15 a further device according to one embodiment.

FIG. 15 shows a further device 1400, according to one embodiment, for processing a filament 201 in a process stream 1409, thereby obtaining a processed filament 410. The device 1400 of FIG. 15 is the same as the device 1400 of FIG. 14, except for including only a single laser (first processing beam source 1404). In order to, nevertheless, allow for simultaneously processing first and further sections of two different segments of the filament 201 as described in the context of FIG. 14, the device of FIG. 15 includes a beam splitter 1501 as processing beam distribution element. Accordingly, the first processing beam source 1404 is designed and arrange to provide a first processing beam via the beam splitter 1501 onto a first section of a first segment of the filament 201 for processing the filament 201 by interaction of the first processing beam with the first section of the first segment, and to provide a further processing beam via the beam splitter 1501 onto a further section of a further segment of the filament 201 for processing the filament 201 by interaction of the further processing beam with the further section of the further segment.

FIG. 16 shows an electrical device 1600 according to one embodiment. The electrical device 1600 comprises a 2 cm long part of the processed filament 410, obtained by the process 100 of FIG. 7, wherein the part includes the first through fourth segments. Here, the electrical device 1600 is a medical device and the part of the processed filament 410 is a component of an electrochemical sensor.

FIG. 17a) shows an illustration of parallel uni-directional processing. What is shown is a part of a filament 201, including a segment 204. Further, linear sweeps 1701 (so-called lines) of a first multitude of linear sweeps (so-called pass) are depicted by arrows which show a sweeping direction. Here, the linear sweeps 1701 are conducted in the same direction. The linear sweeps 1701 of the first multitude of linear sweeps are oriented in parallel to a length of the filament 201, as oriented in the segment 204. Further, a distance 1702 between the linear sweeps 1701 (so-called pitch) is depicted.

FIG. 17b) shows an illustration of parallel bi-directional processing. What is shown is a part of a filament 201, including a segment 204. Further, linear sweeps 1701 (so-called lines) of a first multitude of linear sweeps (so-called pass) are depicted by arrows which show a sweeping direction. Here, a first fraction 1703 of the linear sweeps 1701 of the first multitude of linear sweeps is conducted in a first direction, wherein a further fraction 1704 of the linear sweeps 1701 of the first multitude of linear sweeps is conducted in a further direction, which is opposite to the first direction. The linear sweeps 1701 of the first multitude of linear sweeps are oriented in parallel to a length of the filament 201, as oriented in the segment 204. Further, a distance between the linear sweeps 1702 (so-called pitch) is depicted.

Figures 17C, 17D:
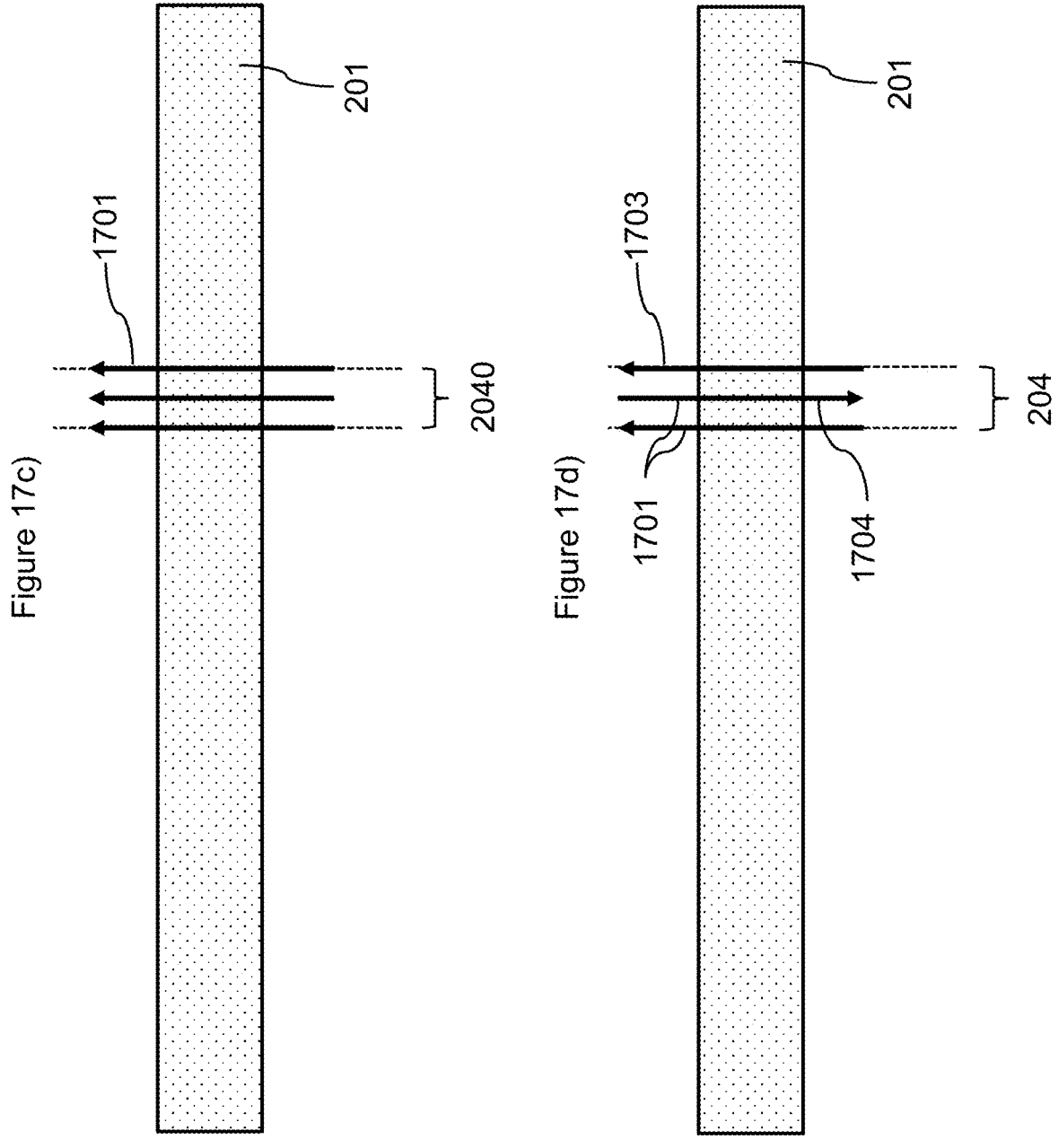
FIG. 17*c*) an illustration of perpendicular uni-directional processing.
FIG. 17*d*) an illustration of perpendicular bi-directional processing.

FIG. 17c) shows an illustration of perpendicular uni-directional processing. What is shown is a part of a filament 201, including a segment 204. Further, linear sweeps 1701 (so-called lines) of a first multitude of linear sweeps (so-called pass) are depicted by arrows which show a sweeping direction. Here, the linear sweeps 1701 are conducted in the same direction. The linear sweeps 1701 of the first multitude of linear sweeps are oriented perpendicular to a length of the filament 201, as oriented in the segment 204.

FIG. 17d) shows an illustration of perpendicular bi-directional processing. What is shown is a part of a filament 201, including a segment 204. Further, linear sweeps 1701 (so-called lines) of a first multitude of linear sweeps (so-called pass) are depicted by arrows which show a sweeping direction. Here, a first fraction 1703 of the linear sweeps 1701 of the first multitude of linear sweeps is conducted in a first direction, wherein a further fraction 1704 of the linear sweeps 1701 of the first multitude of linear sweeps is conducted in a further direction, which is opposite to the first direction. The linear sweeps 1701 of the first multitude of linear sweeps are oriented in parallel to a length of the filament 201, as oriented in the segment 204.

Figure 18:
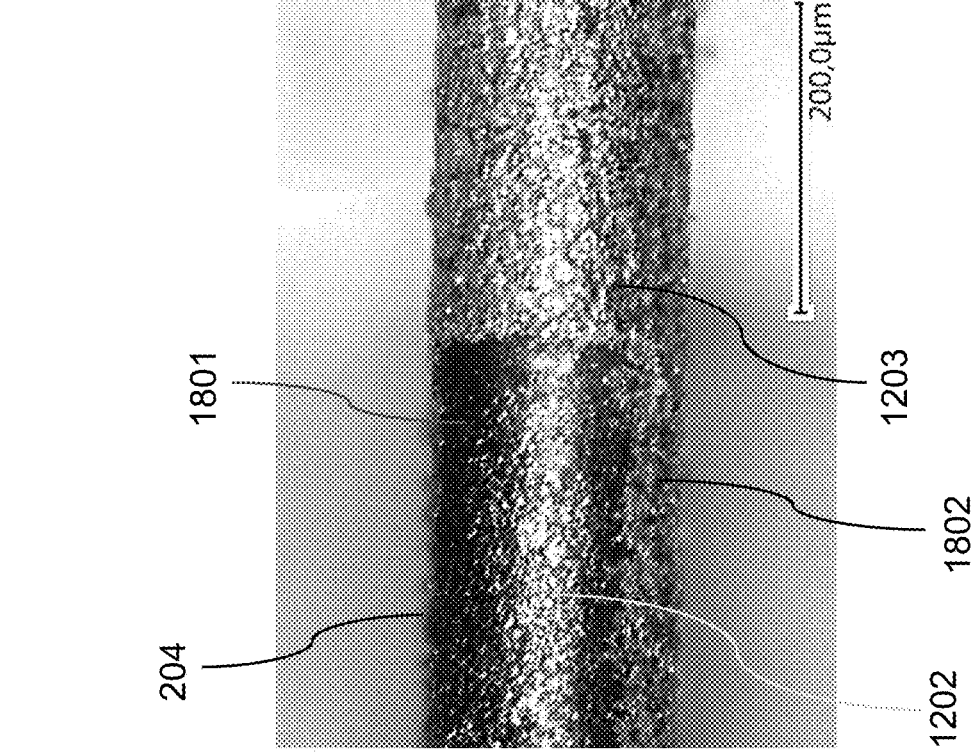
FIG. 18 an optical microscope image of a processed wire.

FIG. 18 shows an optical microscope image of a processed filament 410 which is a processed wire. This wire is of the structure shown in FIG. 12. A segment 204 of the wire is shown. In a processed section 1801 of the segment 204, the second layer 1203 has been ablated, whereas in an unprocessed section 1802 of the segment the second layer 1203 has not been removed. In the processed section 1801, the first layer 1202 has been laid open.

Figure 19:
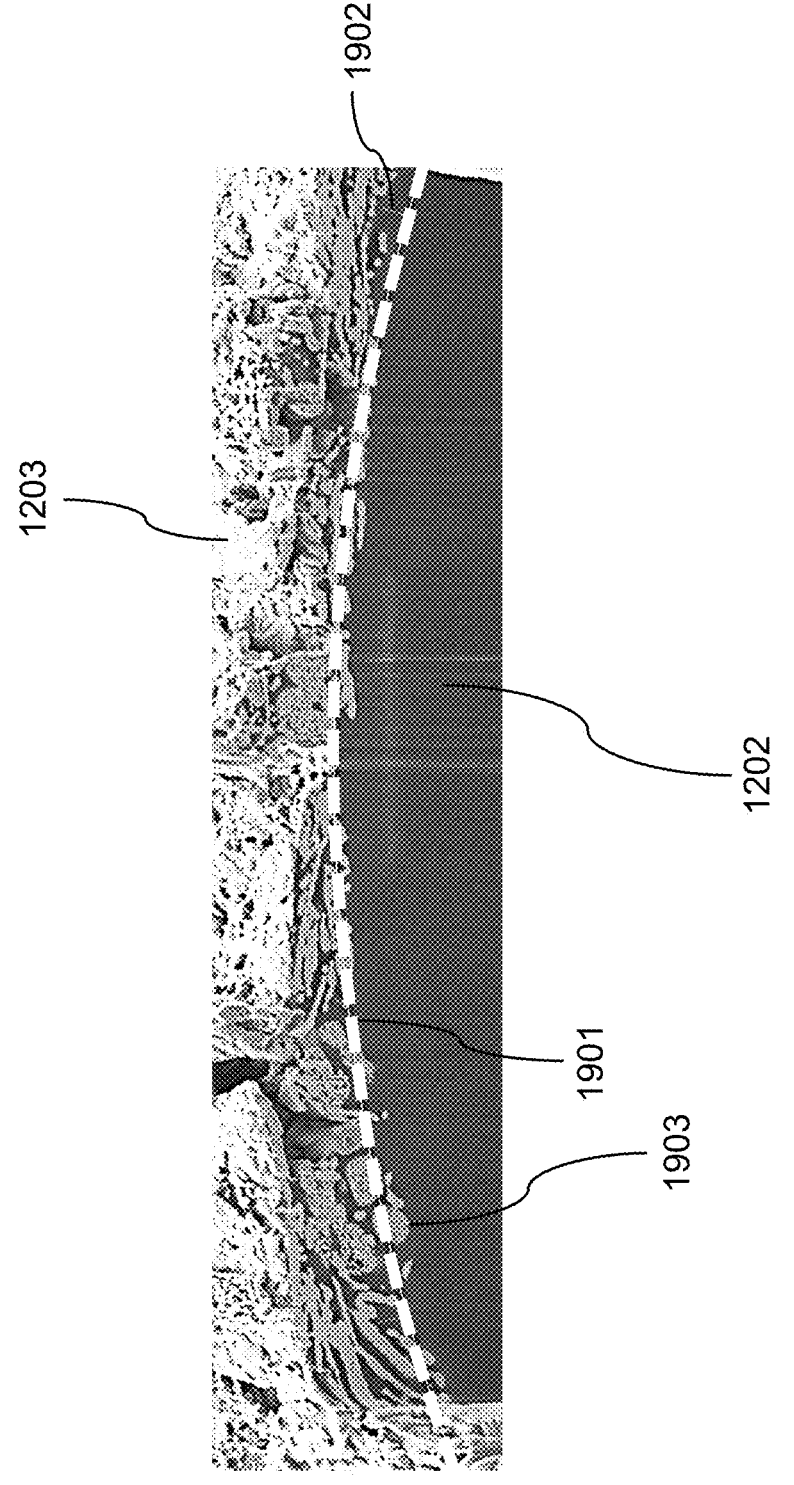
FIG. 19 a focussed-ion-beam image of a cross-section of a wire for determining a roughness of a surface of a first layer of the wire.

FIG. 19 shows a focussed-ion-beam image of a cross-section of a wire for determining a roughness of a surface 1903 of a first layer 1202 of the wire. What can be seen is an interface between a first layer 1202, which is a PU-layer, and a second layer 1203, which is an Ag/AgCl-layer. This interface is at an outer lateral surface 1903 of the first layer 1202. A circle 1901 has been drawn into the image as described above in the test methods section. Further, a distance 1902 between the circle 1901 and the surface 1903 of the first layer 1202 is depicted at equidistant positions along the circle 1101.

Figure 20:
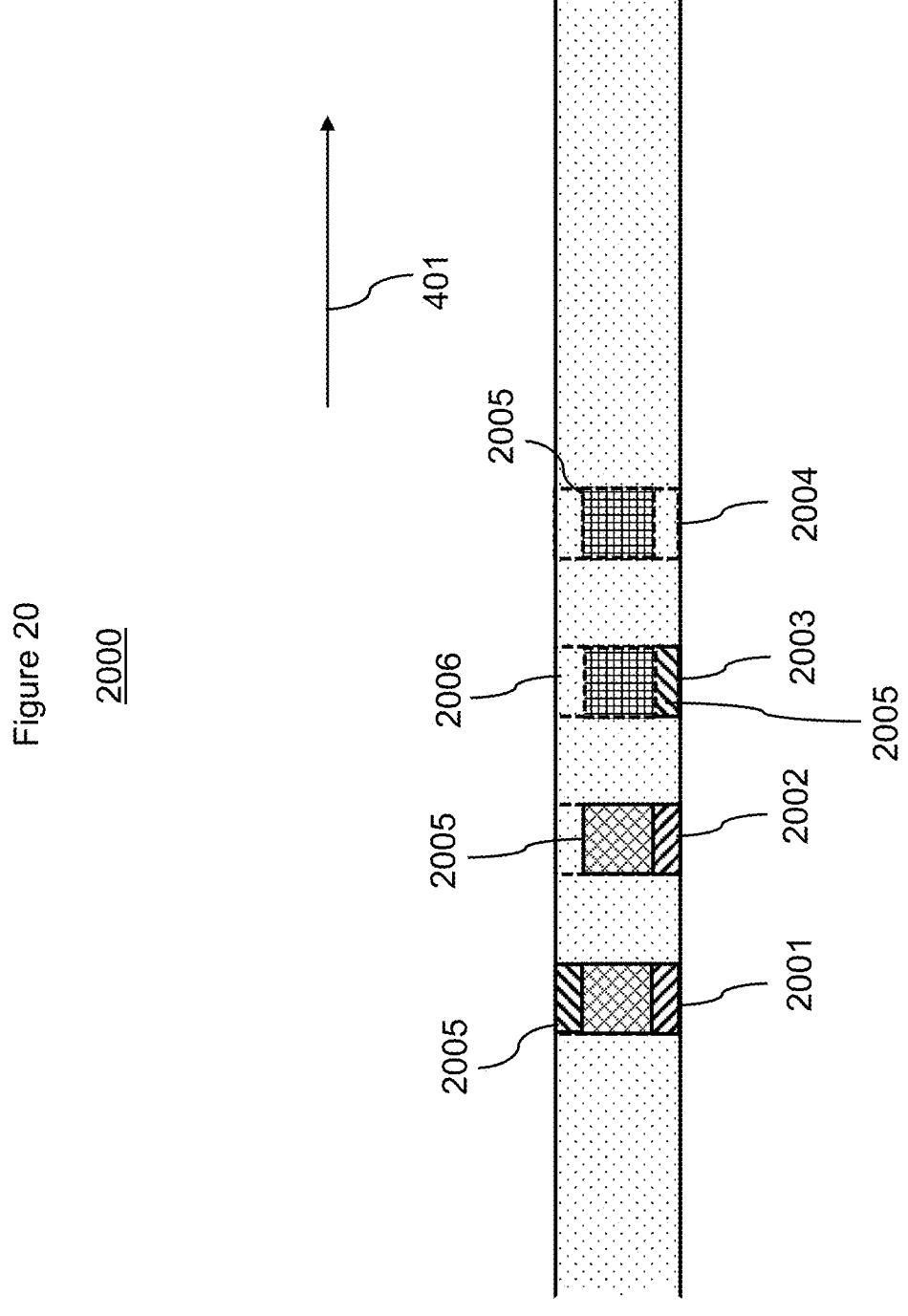
FIG. 20 a side view of a filament according to one embodiment.

FIG. 20 shows a side view of a filament 2000 according to one embodiment. This filament 2000 is of the structure shown in FIG. 12. The filament 2000 comprises 4 segments 2001 to 2004 which follow one another in a longitudinal direction 401 of the filament 2000. Each segment 2001 to 2004 consists of 4 sections which are disposed circumferentially around the filament 2000. The first segment 2001 comprises exactly 4 sections 2005 which have been processed segment. One of these is in the backside of the filament 2000 in the figure. The second segment 2002 comprises exactly 3 sections 2005 which have been processed (one on the backside). The third segment 2003 comprises exactly 2 sections 2005 which have been processed (one on the backside depicted by dashed lines). The fourth segment 2004 comprises exactly 1 section 2005 which has been processed. This section 2005 is on the backside of the filament 2000 and depicted by dashed lines. Hence, from the first 2001 to the fourth segment 2004, the segments comprise an increasing number of sections 2006 which have not been processed. From each section 2005 that has been processed the second layer 1203 of the wire has been removed by laser ablation.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

The invention claimed is:

1. A method for preparing a processed filament, the method comprising:
   a) providing a filament, which comprises a multitude of segments, which follow one another in a longitudinal direction of the filament,
      wherein each of the segments of the multitude of segments comprises a multitude of sections, which are disposed circumferentially around the filament; and
   b) processing sections of the filament in a number of processing steps, thereby obtaining the processed filament;
   wherein in each of n processing steps a number of sections of a number of different segments of the filament is processed;
   wherein n defines the number of processing steps;
   wherein m defines the number of sections and the number of different segments of the filament;
   wherein i denotes a single processing step of the n processing steps, and i is an integer from 1 to n;
   wherein j denotes a single section of the m sections, and j is an integer from 1 to m;

wherein for each integer i in the range from 1 to n, the $i^{th}$ processing step comprises, for each integer j in the range from 1 to m, processing the $j^{th}$ section of the $(i+j-1)^{th}$ segment;
wherein n and m are integers that are independent from one another, and are each at least 2;
wherein each $j^{th}$ section processed in the $i^{th}$ process step is at a different circumferential location of the filament; and
wherein the processing of the sections comprises, in each case, an interaction of the respective section with at least one processing beam;
wherein the filament comprises:
   a. a core, including the first metal,
   b. a first layer which
      i. is superimposed on the core, and
      ii. comprises a polymer, and
   c. a second layer which
      i. is superimposed on the first layer, and
      ii. comprises a second metal;
wherein the processing in the processing steps comprises at least partially removing the second layer from the sections of the segment of the multitude of segment;
wherein between each of two consecutive processing steps the filament is moved in a direction of its length.

2. The method of claim 1, wherein, in each $i^{th}$ processing step, the processing of the $1^{st}$ to $m^{th}$ sections is conducted at least in temporal overlap with one another.

3. The method of claim 1, wherein n equals m.

4. The method of claim 1, wherein the sum of the surface areas of the sections of a segment, which are processed in the process step b), equals the surface area of an outer surface of this segment.

5. The method of claim 1, wherein n or m or each of both is at least 3.

6. The method of claim 1, wherein the processing in the processing steps is a subtractive process.

7. The method of claim 1, wherein the filament is one selected from the group consisting of a wire, a cable, and a fiber, or a combination of at least two thereof.

8. The method of claim 1, wherein the at least one processing beam is at least one laser beam.

9. The method of claim 1, wherein the process is performed as a reel-to-reel-process.

\* \* \* \* \*